(12) United States Patent
Kotenko et al.

(10) Patent No.: US 11,292,823 B2
(45) Date of Patent: Apr. 5, 2022

(54) TYPE I AND TYPE III INTERFERON FUSION MOLECULES AND METHODS FOR USE THEREOF

(71) Applicant: RUTGERS, THE STATE UNIVERSITY OF NEW JERSEY, New Brunswick, NJ (US)

(72) Inventors: Sergei V. Kotenko, East Brunswick, NJ (US); Joan Durbin, New Brunswick, NJ (US); Viralkumar Rameshkumar Davra, Keasbey, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 64 days.

(21) Appl. No.: 16/604,666

(22) PCT Filed: May 1, 2018

(86) PCT No.: PCT/US2018/030370
§ 371 (c)(1),
(2) Date: Oct. 11, 2019

(87) PCT Pub. No.: WO2018/204312
PCT Pub. Date: Nov. 8, 2018

(65) Prior Publication Data
US 2020/0071375 A1  Mar. 5, 2020

Related U.S. Application Data

(60) Provisional application No. 62/492,373, filed on May 1, 2017.

(51) Int. Cl.

| | | |
|---|---|---|
| *C07K 14/56* | (2006.01) | |
| *C07K 14/565* | (2006.01) | |
| *A61K 38/00* | (2006.01) | |
| *A01N 37/18* | (2006.01) | |
| *C07K 14/57* | (2006.01) | |

(52) U.S. Cl.
CPC .............. *C07K 14/56* (2013.01); *A01N 37/18* (2013.01); *C07K 14/565* (2013.01); *C07K 14/57* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 5,939,286 A | 8/1999 | Johnson et al. ........... 435/69.51 |
| 9,051,369 B2 | 6/2015 | Lowenthal et al. . C07K 16 249 |
| 2006/0024269 A1 | 2/2006 | Doyle et al. ................. 424/85.2 |

FOREIGN PATENT DOCUMENTS

| CN | 102212539 | 10/2011 |
| CN | 106674354 | 5/2017 |
| WO | 03/016472 | 2/2003 |
| WO | 2015/056125 | 4/2015 |
| WO | 2019/023156 | 1/2019 |

OTHER PUBLICATIONS

Extended European Search Report in Application No. 18793791.7 dated Feb. 26, 2020.
Chi et al. "Alpha and Lamda Interferon Together Mediate Suppression of CD4 T Cells Induced by Respiratory Synctial Virus" Journal of Virology 2006 80(10):5032-5040.
Voigt et al. "Kinetic Differences and Synergistic Antiviral Effects Between Type I and Type III Interferon Signaling Indicate Pathway Independence" Journal of Interferon and Cytokine Research 2015 35(9):734-747.
Zhao et al. "Construction and phosphorylation of a fusion proteinHu-IFN-αA/γ" Analytical Biochemistry 1989 178(2):342-347.
Fusion Protein Sequence, SEQ ID No. 50 dated Mar. 21, 2019.
Bach et al. "The IFN gamma receptor: a paradigm for cytokine receptor signaling" Annu. Rev. Immunol. 1997 15:563-91.
Biron C.A. "Interferons alpha and beta as immune regulators—a new look" Immunity 2001 14(6):661-4.
Boehm et al. "Cellular responses to interferon—gamma" Annu. Rev. Immunol. 1997 15:749-95.
Dalton et al. "Multiple defects of immune cell function in mice with disrupted interferon—gamma genes" Science 1993 259(5102):1739-42.
Donnelly et al. "The expanded family of class II cytokines that share the IL-10 receptor-2 (IL-10R2) chain" J. Leukoc. Biol. 2004 76(2):314-21.
Donnelly, R.P. & Kotenko, S.V. "Interferon-lambda: a new addition to an old family" J. Interferon Cytokine Res. 2010 30:555-64.
Dorman et al. "Clinical features of dominant and recessive interferon gamma receptor 1 deficiencies" Lancet 2004 364(9451):2113-21.
Hardy et al. "Characterization of the type I interferon locus and identification of novel genes" Genomics 2004 84(2):331-45.
Hör et al. "The T-cell lymphokine interleukin-26 targets epithelial cells through the interleukin-20 receptor 1 and interleukin-10 receptor 2 chains" J. Biol. Chem. 2004 279(32):33343-51.
Huang et al. "Immune response in mice that lack the interferon—gamma receptor" Science 1993 259(5102):1742-5.
Hwang et al. "A null mutation in the gene encoding a type I interferon receptor component eliminates antiproliferative and antiviral responses to interferons alpha and beta and alters macrophage responses" Proc. Natl. Acad. Sci. USA 1995 92(24):11284-8.

(Continued)

*Primary Examiner* — Gary B Nickol
*Assistant Examiner* — Jegatheesan Seharaseyon
(74) *Attorney, Agent, or Firm* — Licata & Tyrrell P.C.

(57) ABSTRACT

Fusion molecules composed of a type I interferon protein or portion thereof and a type III interferon protein or portion thereof, pharmaceutical compositions containing the fusion molecules, and methods for their use in inhibiting infection, inhibiting or treating cancer, inducing signaling of transcription of IFN-stimulated genes through an IFN-αR2 chain in a subject suffering from an infection which degrades or downregulates an IFN-αR1 chain, and treating various diseases or conditions are provided.

12 Claims, 25 Drawing Sheets
Specification includes a Sequence Listing.

(56) References Cited

OTHER PUBLICATIONS

Kotenko S.V. "The family of IL-10-related cytokines and their receptors: related, but to what extent?" Cytokine Growth Factor Rev. 2002 13(3):223-40.
Kotenko et al. "Identification and functional characterization of a second chain of the interleukin-10 receptor complex" EMBO J. 1997 16(19):5894-903.
Kotenko et al. "Identification of the functional interleukin-22 (IL-22) receptor complex: the IL-10R2 chain (IL-10Rbeta) is a common chain of both the IL-10 and IL-22 (IL-10-related T cell-derived inducible factor, IL-TIf) receptor complexes" J. Biol. Chem. 2001 276(4):2725-32.
Kotenko et al. "IFN-lambdas mediate antiviral protection through a distinct class II cytokine receptor complex" Nat. Immunol. 2003 4(1):69-77.
Kotenko, S.V. & Langer, J.A. "Full house: 12 receptors for 27 cytokines" Int. Immunopharmacol. 2004 4(5):593-608.
LaFleur et al. "Interferon-kappa, a novel type I interferon expressed in human keratinocytes" J. Biol. Chem. 2001 276(43):39765-71.
Langer et al. "The Class II cytokine receptor (CRF2) family: overview and patterns of receptor-ligand interactions" Cytokine Growth Factor Rev. 2004 15(1):33-48.
Lasfar et al. "IFN Therapy in TIB 75 HCC Model: Combination of IFN-lambda and IFN-alpha Induces Complete Remission" Hepatology 2008 48(4S):394A-395A.
Lasfar et al. "Concerted action of IFN-α and IFN-λ induces local NK cell immunity and halts cancer growth" Oncotarget 2016 7(31):49259-49257.
Le Bon, A. & Tough, T.F. "Links between innate and adaptive immunity via type I interferon" Curr. Opin. Immunol. 2002 14(4):432-6.
Levy, D.E. & Garcia-Sastre, A. "The virus battles: IFN induction of the antiviral state and mechanisms of viral evasion" Cytokine Growth Factor Rev. 2001 12(2-3):143-56.
Lu et al. "Targeted disruption of the interferon-gamma receptor 2 gene results in severe immune defects in mice" Proc. Natl. Acad. Sci. USA 1998 95(14):8233-8.
Müller et al. "Functional role of type I and type II interferons in antiviral defense" Science 1994 264(5167):1918-21.
Novelli, F. & Casanova, J-L. "The role of IL-12, IL-23 and IFN-gamma in immunity to viruses" Cytokine Growth Factor Rev. 2004 15(5):367-77.
Pestka et al. "The interferon gamma (IFN-gamma) receptor: a paradigm for the multichain cytokine receptor" Cytokine Growth Factor Rev. 1997 8(3):189-206.
Pestka et al. "Interferons, interferon-like cytokines, and their receptors" Immunol. Rev. 2004 202:8-32.
Pestka et al. "Interleukin-10 and related cytokines and receptors" Annu. Rev. Immunol. 2004 22:929-979.
Prokunina-Olson et al. "A variant upstream of IFNL3 (IL28B) creating a new interferon gene IFNL4 is associated with impaired clearance of hepatitis C virus" Nat. Genet. 2013 45(2):164-71.
Renauld J-C. "Class II cytokine receptors and their ligands: key antiviral and inflammatory modulators" Nat. Rev. Immunol. 2003 3(8):667-76.
Samuel C.E. "Antiviral actions of interferons" Clin. Microbiol. Rev. 2001 14(4):778-809.
Sheikh et al. "Cutting edge: IL-26 signals through a novel receptor complex composed of IL-20 receptor 1 and IL-10 receptor 2" J. Immunol. 2004 172(4):2006-10.
Sheppard et al. "IL-28, IL-29 and their class II cytokine receptor IL-28R" Nat. Immunol. 2003 4(1):63-8.
Steinhoff et al. "Antiviral protection by vesicular stomatitis virus-specific antibodies in alpha/beta interferon receptor-deficient mice" J. Virol. 1995 69(4):2153-8.
Xie et al. "Interleukin (IL)-22, a novel human cytokine that signals through the interferon receptor-related proteins CRF2-4 and IL-22R" J. Biol. Chem. 2000 275(40):31335-9.
International Search Report and Written Opinion in PCT/US2018/030370 dated Jul. 13, 2018.
International Preliminary Report on Patentability in PCT/US2018/030370 dated Nov. 5, 2019.

```
  1 MALTFALLVA LLVLSCKSSC SVGCDLPQTH SLGSRRTLML LAQMRRISLF SCLKDRHDFG  60
 61 FPQEEFGNQF QKAETIPVLH EMIQQIFNLF STKDSSAAWD ETLLDKFYTE LYQQLNDLEA 120
121 CVIQGVGVTE TPLMKEDSIL AVRKYFQRIT LYLKEKKYSP CAWEVVRAEI MRSFSLSTNL 180
181 QESLRSKESR RASGSSGGSS GTSGSSGGSS GTSTDPVPTS KPTPTGKGCH IGRFKSLSPQ 240
241 ELASFKKARD ALEESLKLKN WSCSSPVFPG NWDLRLLQVR ERPVALEAEL ALTLKVLEAA 300
301 AGPALEDVLD QPLHTLHHIL SQLQACIQPQ PTAGPRPRGR LHHWLHRLQE APKKESAGCL 360
361 EASVTFNLFR LLTRDLKYVA DGNLCLRTST HPEST*
```

FIG. 12

```
  1 MALTFALLVA LLVLSCKSSC SVGCDLPQTH SLGSRRTLML LAQMRRISLF SCLKDRHDFG   60
 61 FPQEEFGNQF QKAETIPVLH EMIQQIFNLF STKDSSAAWD ETLLDKFYTE LYQQLNDLEA  120
121 CVIQGVGVTE TPLMKEDSIL AVRKYFQRIT LYLKEKKYSP CAWEVVRAEI MRSFSLSTNL  180
181 QESLRSKESR RASGSSGGSS GTSGSSGGSS GTSTDPVARL RGALPDARGC HIAQFKSLSP  240
241 QELQAFKRAK DALEESLLLK DCKCRSRLFP RTWDLRQLQV RERPVALEAE LALTLKVLEA  300
301 SADTDPALGD VLDQPLHTLH HILSQLRACI QPQPTAGPRT RGRLHHWLYR LQEAPKKESP  360
361 GCLEASVTFN LFRLLTRDLN CVASGDLCV*
```

FIG. 13

```
  1 MTNKCLLQIA LLLCFSTTAL SMSYNLLGFL QRSSNFQCQK LLWQLNGRLE YCLKDRMNFD  60
 61 IPEEIKQLQQ FQKEDAALTI YEMLQNIFAI FRQDSSSTGW NETIVENLLA NVYHQINHLK 120
121 TVLEEKLEKE DFTRGKLMSS LHLKRYYGRI LHYLKAKEYS HCAWTIVRVE ILRNFYFINR 180
181 LTGYLRNASG SSGGSSGTSG SSGGSSGTST DPVARLRGAL PDARGCHIAQ FKSLSPQELQ 240
241 AFKRAKDALE ESLLLKDCKC RSRLFPRTWD LRQLQVRERP VALEAELALT LKVLEASADT 300
301 DPALGDVLDQ PLHTLHHILS QLRACIQPQP TAGPRTRGRL HHWLYRLQEA PKKESPGCLE 360
361 ASVTFNLFRL LTRDLNCVAS GDLCV*
```

FIG. 14

```
  1 MARLCAFLMT LLVMSYWSTC SLG CDLPQTH NLRNKRALTL LVQMRRLSP  LSCLKDRKDFR   60
 61 FPQEKVDAQQ IQNAQAIPVL QELTQQVLNI FTSKDSSAAW DASLLDSFC  NDLHQQLNDLK  120
121 ACVMQEVGVQ EPPLTQEDYL LAVRTYFHRI TVYLREKKRS PCAWEVVRA  EVWRAMYSSAK  180
181 LPARLSEEKE ASGSSGGSSG TSGSSGGSSG TSTD PVPRAT RLPVEAKDC  HIAQFKSLSPK  240
241 ELQAFKKAKD AIEKRLLEKD MRCSSHLISR AWDLKQLQVQ ERPKALQAE  VALTLKVWENM  300
301 TDSALATILG QPLHTLSHIH SQLQTCTQLQ ATAEPKPPSR RLSRWLHRL  QEAQSKETPGC  360
361 LEDSVTSNLF RLLTRDLKCV ASGDQCV*
```

FIG. 21

```
  1 MNNRWILHAA FLLCFSTTAL S NYKQLQLQ ERTNIRKCQE LLEQLNGKIN LTYRADFKIP   60
 61 MEMTEKMQKS YTAFAIQEML QNVFLVFRNN FSSTGWNETI VVRLLDELHQ QTVFLKTVLE  120
121 EKQEERLTWE MSSTALHLKS YYWRVQRYLK LMKYNSYAWM VVRAEIFRNF LIIRRLTRNF  180
181 QN ASGSSSGGS SGTSGSSGGS SGTSTDP VPR ATRLPVEAKD CHIAQEKSLS PKELQAFKKA  240
241 KDAIEKRLLE KDMRCSSHLI SRAWDLKQLQ VQERPKALQA EVALTLKVWE NMTDSALATI  300
301 LGQPLHTLSH IHSQLQTCTQ LQATAEPKPP SRRLSRWLHR LQEAQSKETP GCLEDSVTSN  360
361 LFRLLTRDLK CVASGDQCV*
```

FIG. 22

TYPE I AND TYPE III INTERFERON FUSION MOLECULES AND METHODS FOR USE THEREOF

This patent application is the National Stage of International Application No. PCT/US2018/030370 filed May 1, 2018, which claims the benefit of priority from U.S. Provisional Application Serial No. 62/492,373 filed May 1, 2017, the content of each of which is herein incorporated by reference in its entirety.

BACKGROUND

Interferons (IFNs) are key cytokines in the establishment of a multifaceted antiviral response. Three distinct types of IFNs are now recognized (type I, II, and III) based on their structural features, receptor usage and biological activities. Although all IFNs are important mediators of antiviral protection, their roles in antiviral defense vary. Type I IFNs (IFN-α/β/ω/ε/κ in humans) possess strong intrinsic antiviral activity, and are able to induce a potent antiviral state in a wide variety of cells (Levy & Garcia-Sastre (2001) *Cytokine Growth Factor Rev.* 12(2-3): 143-56; Samuel (2001) *Clin. Microbiol. Rev.* 14(4):778-809). The essential role of the type I IFNs in the induction of antiviral resistance has been clearly demonstrated using type I IFN receptor knockout mice because such animals are highly susceptible to many viral infections (Müller, et al. (1994) *Science* 264(5167): 1918-21; Hwang, et al. (1995) *Proc. Natl. Acad. Sci. USA* 92(24):11284-8; Steinhoff, et al. (1995) *J. Virol.* 69(4):2153-8). In contrast, studies with IFN-γ and IFN-γ receptor knock-out mice (Dalton, et al. (1993) *Science* 259(5102): 1739-42; Huang, et al. (1993) *Science* 259(5102):1742-5; Lu, et al. (1998) *Proc. Natl. Acad. Sci. USA* 95(14):8233-8) as well as analysis of humans who possess inherited genetic mutations of the IFN-γ receptor (Dorman, et al. (2004) *Lancet* 364(9451):2113-21; Novelli & Casanova (2004) *Cytokine Growth Factor Rev.* 15(5):367-77) revealed that antiviral activity is not the primary biological function of IFN-γ.

IFN-γ is classified as a Thi-type cytokine that stimulates cell-mediated immune responses that are critical for the development of host protection against pathogenic intracellular microorganisms such as *Mycobacterium tuberculosis* (Bach, et al. (1997) *Annu. Rev. Immunol.* 15:563-91; Boehm, et al. (1997) *Annu. Rev. Immunol.* 15:749-95; Pestka, et al. (1997) *Cytokine Growth Factor Rev.* 8(3):189-206). IFN-γ also plays a central role in the development of antitumor immune responses, and it can amplify the induction of antiviral activity by IFN-α or -β, or -λ. Therefore, type I and type II IFNs often work together to activate a variety of innate and adaptive immune responses that result in the induction of effective antitumor immunity and the elimination of viral infections (Biron (2001) *Immunity* 14(6):661-4; Le Bon & Tough (2002) *Curr. Opin. Immunol.* 14(4):432-6; Pestka, et al. (2004) *Immunol. Rev.* 202:8-32).

IFNs are part of the larger family of class II cytokines that also includes six IL-10-related cytokines: IL-10, IL-19, IL-20, IL-22, IL-24, and IL-26 (Kotenko (2002) *Cytokine Growth Factor Rev.* 13(3):223-40; Renauld (2003) *Nat. Rev. Immunol.* 3(8):667-76; Pestka, et al. (2004) *Annu. Rev. Immunol.* 22:929-979) as well as several viral IL-10-related cytokines (Kotenko & Langer (2004) *Int. Immunopharmacol.* 4(5):593-608). IFNs and the IL-10-related cytokines can be grouped into the same family because they all signal via receptors that share common motifs in their extracellular domains. These receptors include the class II cytokine receptor family (CRF2). Consequently, IFNs and the IL-10-related cytokines are sometimes referred to as "CRF2 cytokines." The type I IFN family in humans is composed of 13 IFN-α species and a single species of IFN-β, IFN-κ, IFN-ω, and IFN-ε (LaFleur, et al. (2001) *J. Biol. Chem.* 276(43): 39765-71; Hardy, et al. (2004) *Genomics* 84(2):331-45; Langer, et al. (2004) *Cytokine Growth Factor Rev.* 15(1): 33-48; Pestka, et al. (2004) *Immunol. Rev.* 202:8-32). There is only one type II IFN in humans known as IFN-γ. Although the tertiary structure of IFN-γ resembles that of IL-10, its primary structure has diverged the most from all of the CRF2 ligands. The most recent addition to the CRF2 family, the type III IFNs or IFN-λs, demonstrate structural features of the IL-10-related cytokines but also induce antiviral activity in a variety of target cells, which supports their functional classification as a new type of IFNs (Kotenko, et al. (2003) *Nat. Immunol.* 4(1):69-77; Sheppard, et al. (2003) *Nat. Immunol.* 4(1):63-8). In humans, three distinct but closely related IFN-λ proteins, IFN-λ1, -λ2, and -λ3 (also known as IL-29, IL-28A, and IL-28B, respectively) were initially identified. In 2013, the type III IFN family was extended with an additional member IFN-λ4 protein, which shares only limited homology with IFN-λ1, -λ2, and -λ3 (Prokunina-Olson, et al. (2013) *Nat. Genet.* 45(2):164-71). Phylogenetically, the IFN-λ genes reside somewhere between the type I IFN and IL-10 gene families (Donnelly & Kotenko (2010) *J. Interferon Cytokine Res.* 30:555-64). Amino acid sequence comparisons show that the type III IFNs exhibit about ~5%-18% identity with either type I IFNs or the IL-10-related cytokines.

The IFN-λ proteins bind and signal through a receptor complex composed of the unique IFN-λR1 chain (also known as IL-28RA) and the shared IL-10R2 chain which is also a part of the receptor complexes for IL-10, IL-22, and IL-26 (see FIG. 1 and Kotenko, et al. (1997) *EMBO J.* 16(19):5894-903; Kotenko, et al. (2001) *J. Biol. Chem.* 276(4):2725-32; Xie, et al. (2000) *J. Biol. Chem.* 275(40): 31335-9; Donnelly, et al. (2004) *J. Leukoc. Biol.* 76(2):314-21; Hör, et al. (2004) *J. Biol. Chem.* 279(32):33343-51; Sheikh, et al. (2004) *J. Immunol.* 172(4):2006-10). In contrast, all type I IFNs exert their biological activities through a heterodimeric receptor complex composed of the IFN-αR1 (IFNAR1) and IFN-αR2 (IFNAR2) chains (see FIG. 1), and type II IFN (IFN-γ) engages the IFN-γR1 (IFNGR1) and IFN-γR2 (IFNGR2) chains to assemble its functional receptor complex. Although the IFN-λs do not use the IFN-α receptor complex for signaling, signaling through either IFN-λ or IFN-α receptor complexes results in the activation of the same Jak-STAT signal transduction cascade (see FIG. 1).

IFN-λ binds initially to the IFN-λR1 chain, and the binary complex formed by the association of IFN-λ with the IFN-λR1 chain causes a rapid conformational change that facilitates recruitment of the second receptor chain, IL-10R2, to the complex. Once assembly of the ternary complex is complete, the receptor-associated *Janus* tyrosine kinases, Jak1 and Tyk2, mediate trans-phosphorylation of the receptor chains which results in the formation of phosphotyrosine-containing peptide motifs on the intracellular domain (ICD) of the IFN-λR1 chain that provide transient docking sites for latent preformed cytosolic STAT proteins, including STAT1 and STAT2. Signaling through type I (IFN-α/β) or type III (IFN-λ) IFN receptor complexes results in the formation of a transcription factor complex known as IFN-stimulated gene factor 3 (ISGF3). This complex is composed of three proteins, STAT1, STAT2, and IFN regulatory factor-9 (IRF-9) (also known as ISGF3γ or p48).

Once assembled, ISGF3 then translocates to the nucleus where it binds to IFN-stimulated response elements in the promoters of various IFN-stimulated genes (ISGs). Consequently, the biological activities induced by either type I or type III IFNs are very similar, including induction of antiviral activity, up-regulation of major histocompatibility complex (MHC) class I antigen expression on many cell types, and anti-tumor activity. Moreover, it has been shown that coadministration of IFN-α and IFN-λ provides a synergistic antitumor effect in a mouse model of hepatocellular carcinoma (Lasfar, et al. (2008) Hepatology 48(4S):394A-395A; Lasfar, et al. (2016) Oncotarget 7(31):49259-49257).

SUMMARY OF THE INVENTION

An aspect of the present invention relates to fusion molecules composed of a type I IFN protein or portion thereof and a type III IFN protein or portion thereof. In one nonlimiting embodiment, the type I interferon protein molecule of the fusion molecule is interferon alpha, interferon alpha 2 or interferon beta, or a portion thereof. In one nonlimiting embodiment, the type III interferon protein of the fusion molecule is interferon lambda 1, interferon lambda 2 or interferon lambda 3, or a portion thereof. In some nonlimiting embodiments, the fusion molecules further comprise a linker between the type I interferon protein or portion thereof and type III interferon protein or portion thereof and/or a signal peptide at the N-terminus of the fusion molecule.

Another aspect of the present invention relates to pharmaceutical compositions comprising the fusion molecule and a pharmaceutically acceptable carrier.

Another aspect of the present invention relates to a method for inhibiting infection in a subject. The method comprises administering to the subject an effective amount of the fusion molecule. In one nonlimiting embodiment, the fusion molecule targets and inhibits infection in two or more cell types in a subject.

Another aspect of the present invention relates to a method for inhibiting or treating cancer in a subject. The method comprises administering to the subject an effective amount of the fusion molecule.

Another aspect of the present invention relates to a method for inducing signaling leading to transcription of IFN-stimulated genes through an IFN-αR2 chain in a subject suffering from an infection which degrades or downregulates an IFN-αR1 chain. The method comprises administering to the subject an effective amount of the fusion molecule.

Yet another aspect of the present invention relates to a method for treating a disease or condition. The method comprises administering to a subject in need of treatment an effective amount of the fusion molecule thereby treating the subject's disease or condition. In one nonlimiting embodiment, the disease or condition is responsive to interferon treatment. In one nonlimiting embodiment the disease or condition is a viral infection, a fungal infection, a bacterial infection, cancer, an inflammatory disease, or an autoimmune disease.

BRIEF DESCRIPTION OF THE DRAWINGS

FIG. 3B) or IFN-λ2 (1 µg; FIG. 3C).

FIG. 4A) or IFN-λ2 (1 µg; FIG. 4B)

FIG. 12 shows the amino acid sequence of human (h) IFN-α-hIFN-λ1 fusion molecule (SEQ ID NO:51). The signal peptide sequence at the N-terminus is boxed as is the glycine/serine-rich linker.

FIG. 13 shows the amino acid sequence of hIFN-α-hIFN-λ3 fusion molecule (SEQ ID NO:52). The signal peptide sequence at the N-terminus is boxed as is the glycine/serine-rich linker.

FIG. 14 shows the amino acid sequence of hIFN-β-hIFN-λ3 fusion molecule (SEQ ID NO:53). The signal peptide sequence at the N-terminus is boxed as is the glycine/serine-rich linker.

In FIG. 20B, mice were also injected with 50:50 percent ratio of E0771 cells expressing single IFN molecule. FIG. 20C depicts tumor volume in each individual mouse at day 26 after tumor cell implantation.

FIG. 21 shows the amino acid sequence of mouse (m) IFN-α-mIFN-λ2 fusion molecule (SEQ ID NO:54). The signal peptide sequence at the N-terminus is boxed as is the glycine/serine-rich linker.

FIG. 22 shows the amino acid sequence of mIFN-β-mIFN-λ2 fusion molecule (SEQ ID NO:55). The signal peptide sequence at the N-terminus is boxed as is the glycine/serine-rich linker.

DETAILED DESCRIPTION OF THE INVENTION

Disclosed herein are fusion molecules comprising interferon proteins or portions thereof, pharmaceutical compositions containing the fusion molecules, and methods for their use in inhibiting infection, inhibiting or treating cancer, inducing signaling of transcription of IFN-stimulated genes through an IFN-αR2 chain in a subject suffering from an infection which degrades or downregulates an IFN-αR1 chain, and treating various diseases or conditions.

For purposes of the present invention, the terms "fusion protein" and "fusion molecule" are used interchangeably and are meant to encompass polypeptides, proteins and/or molecules made of parts from different sources. Such fusion molecules are created through the joining of two or more genes or fragments thereof that originally coded for separate proteins or portions thereof. Translation of these fused genes or portions thereof results in single or multiple polypeptides with functional properties derived from each of the original proteins. In one nonlimiting embodiment, the fusion molecules or proteins are created artificially by recombinant DNA technology for use in biological research or therapeutics.

For purposes of the present invention, by "portion thereof" it is meant a fragment shorter in length than the full length interferon protein and which maintains at least a portion of the functional activity to the full length protein and/or binding to at least one of the receptor subunits.

Figure 1:
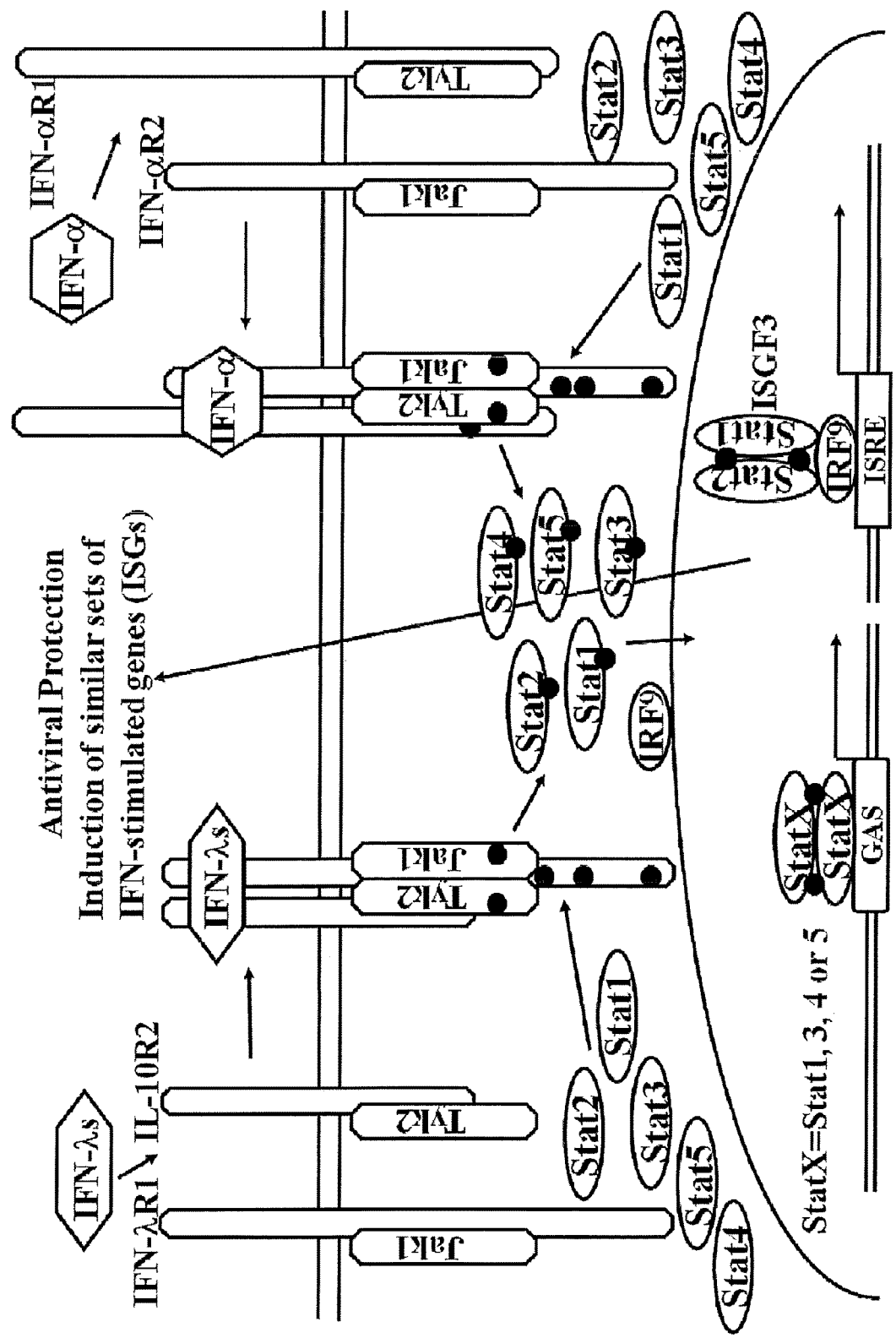
FIG. 1 depicts models of type III IFN (IFN-λ) and type I IFN (IFN-α/β) receptor systems. IFN-λs and type I IFNs use distinct heterodimeric receptor complexes. The IFN-λs engage the unique IFN-λR1 and IL-10R2, whereas IFN-αR1 and IFN-αR2 form the active type I IFN receptor complex. The engagement of IFN-α or IFN-λ receptors results in phosphorylation of receptor-associated JAK kinases JAK1 and Tyk2 and this is followed by phosphorylation of STAT1 and STAT2 that interact with a DNA-binding protein IRF9 leading to the formation of a transcriptional complex designated IFN-stimulated gene factor 3 (ISGF3), which binds to the IFN-stimulated response element (ISRE) and regulates transcription of IFN-stimulated genes (ISGs).
Figure 2:
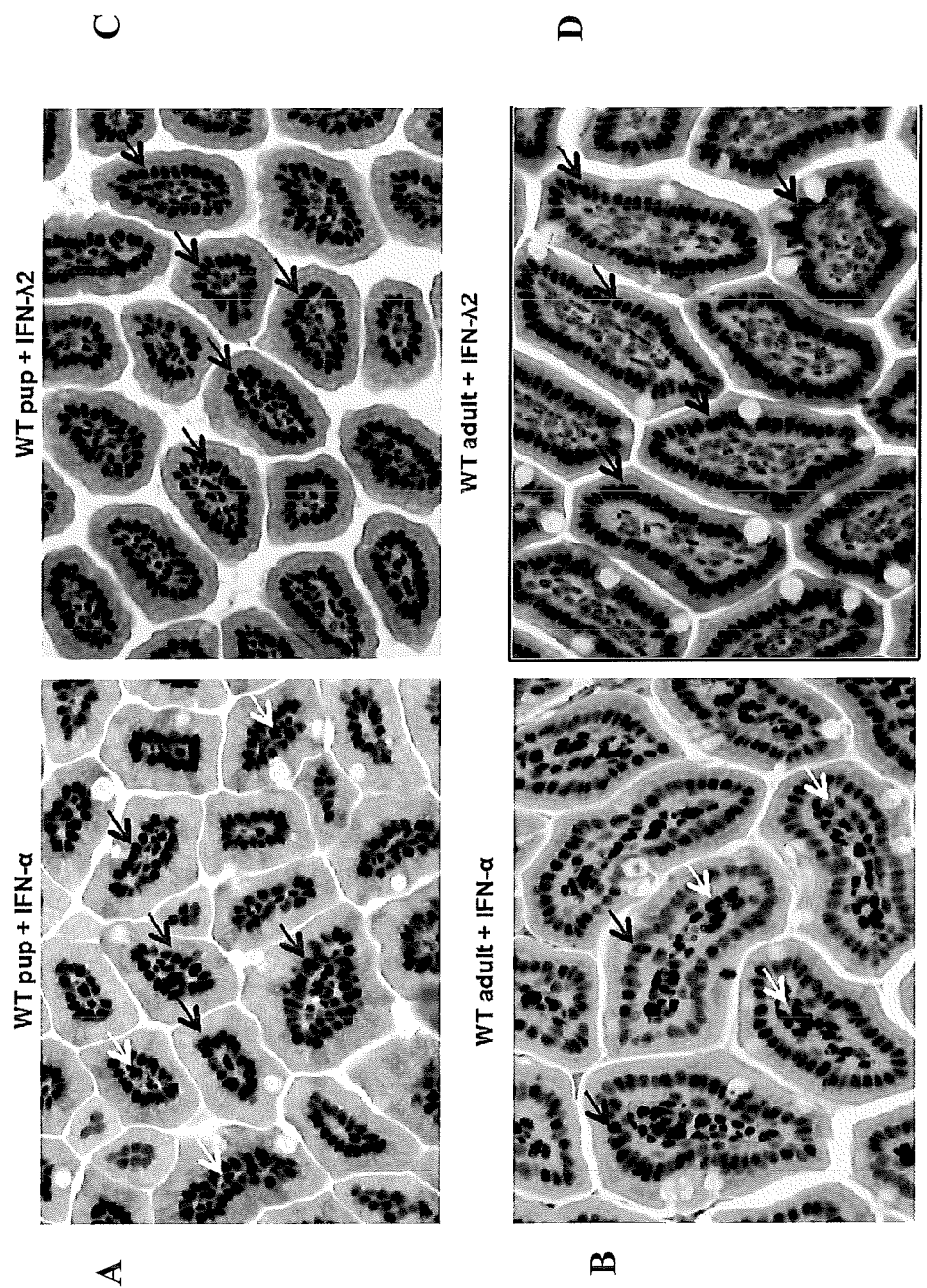
FIGS. 2A, 2B, 2C and 2D show IHC staining of pSTAT1 (pTyr701) in small intestine of wild type (WT) 8-day-old pups or 8-week-old adult mice injected subcutaneously (SQ) with human IFN-αA/D (IFN-α; 1 µg (FIGS. 2A and 2B)) or murine IFN-λ2 (IFN-λ; 1 µg (FIGS. 2C and 2D)). Black arrows indicate nuclear staining of pSTAT1 in IFN-treated epithelial cells and white arrows indicate inflammatory cells within the lamina propria respectively.

Type I IFNs, IFN-α/β are used in the clinic to treat various pathological conditions, including viral infections, cancer and multiple sclerosis (IFN-beta). However, the use of IFN-α/β remains problematic due to low efficacy and a number of significant side effects. Type III IFNs, or IFN-λs, have been shown to possess antiviral and anti-tumor activities comparable to those of type I IFNs in murine models of viral infection and cancer. Although type I and type III IFNs have similar biological activities, they utilize unique IFN type-specific receptor complexes for signaling (FIG. 1). Because receptors for type I and type III IFNs demonstrate distinct patterns of cell type and tissue distribution, these IFNs target both overlapping and distinct IFN type-specific cell populations.

Type I IFN receptors are expressed in most cell types, whereas IFN-λR1 demonstrates a more restricted pattern of expression, limiting responses to type III IFNs primarily to epithelial cells of the respiratory, gastro-intestinal and reproductive tracts (Sommereyns, et al. (2008) *PLoS Pathog.*

4:e1000017; Lasfar, et al. (2006) *Cancer Res.* 66:4468-4477). The unique functional tissue-specificity of the IFN-λ response is due to the cell type-restricted pattern of IFN-λR1 expression; although all cells express receptors for type I IFNs, IFN-λR1 is primarily expressed in epithelial cells and specific subsets of immune cells (Kotenko and Durbin (2017) *J. Biol. Chem.* 292(18):7295-7303). Indeed, it was demonstrated that both type I and type III IFN systems are capable of providing efficient, comparable, and independent antiviral protection in vivo against infections targeting epithelial tissues where receptors for both types of IFNs are expressed (Sheppard, et al. (2003) *Nat. Immunol.* 4:63-68; Kotenko, et al. (2003) *Nat. Immunol.* 4:69-77; Doyle, et al. (2006) *Hepatology* 44:896-906; Ank, et al. (2006) *J. Virol.* 80:4501-4509). However, it has been demonstrated that antiviral protection of intestinal epithelial cells against gastrointestinal (GI) viruses mainly relies on the action of the type III IFN antiviral system (Pott, et al. (2011) *Proc. Natl. Acad. Sci. USA* 108:7944-49; Lin, et al. (2016) PLOS Path. 12:e1005600). These studies revealed that, unlike influenza A virus infection in the lung, mice lacking a functional IFN-λ receptor complex had impaired control of oral rotavirus (RV) infection; the type I IFN system alone was able to provide only a weak protection against rotaviruses, which infect intestinal epithelial cells. Importantly, mice deficient in both type I and type III IFN receptors were more susceptible to RV infection than mice deficient in each IFN receptor (Lin, et al. (2016) PLOS Path. 12:e1005600). Accordingly, systemic administration of IFN-λ or type I IFN was able to induce an antiviral state in intestinal epithelial cells resulting in the suppression of rotavirus replication. However, only type I IFNs protect against hepatotropic viruses. Thus, the type I and type III IFN systems have unique functions in overall antiviral defense. Type I IFNs seem to be required for antiviral protection of liver, endothelial cells, fibroblasts and immune cells where type III IFNs have minimal or no activity. In contrast, the type III IFN system is required for effective antiviral protection of intestinal epithelium that is independent of, and not overlapping with, the type I IFN antiviral system, whereas both types of IFNs can provide efficient and independent antiviral protection in lungs (Mordstein, et al (2010) *J. Virol.* 84:5670-7).

Viral studies demonstrating that type I and type III IFNs target distinct organs and tissues have been confirmed with the use of transgenic reporter mice that have a luciferase reporter gene controlled by Mx2 promoter that is specifically and uniquely induced by type I and type III IFNs (Pulverer, et al. (2010) *J. Virol.* 84:8626). Using such reporter mice, it has been shown that intravenous administration of IFN-λ induced the strongest expression of luciferase in organs with mucosal surfaces such as stomach, small and large intestine, lungs and salivary glands. In contrast, the type I IFN response was strong in liver, spleen, and kidney. Minimal or no response to intravenous-administered type I IFNs was detected in GI tract and salivary glands, whereas lungs were responsive to type I IFNs. Interestingly, in addition to targeting different organs, type I and type III IFNs demonstrated differential kinetics of the response. Whole-body live imaging showed that luciferase expression peaked at 3 hours in response to IFN-β, at 6 hours in response to IFN-α, and at 9 hours in response to IFN-λ injection. In fact, the response to IFN-λ was fast and could be clearly detected in lungs and GI tract at 3 hours and lasted until 24 hours. Therefore, the dominant target organs of type I and type III IFNs as well as kinetics of their action are clearly distinct.

Although intestinal epithelial cells are responsive only to IFN-λ in adult animals, it is not true in neonates, the cohort susceptible to rotavirus-induced diarrheal illness. Optimal protection from rotavirus during neonatal infection required both the IFNLR and the IFNAR, and both IFN pathways are active in the neonatal intestine (Lin, et al. (2016) PLOS Path. 12:e1005600). In FIGS. 2A-2D, IFN signaling was detected 30 minutes following subcutaneous (SQ) injection of IFN-α or IFN-λ. Formalin-fixed paraffin embedded (FFPE) tissues were stained with a monoclonal antibody to tyrosine-phosphorylated STAT1 (pSTAT1). Nuclear localization of pSTAT1 is evidence of signaling through either the IFNAR or IFNLR. In these sections from the intestine of IFN-treated adult mice, nuclear staining of hematopoietic cells within the lamina propria (white arrows) is present following treatment with IFN-α, and only in the intestinal epithelial cells (black arrows) following IFN-λ treatment. However in neonates, intestinal epithelial cells responded well to either IFN-α or IFN-λ as measured by nuclear localization of pSTAT1. All cell lines derived from the intestine that were tested are fully sensitive to both types of IFNs. Thus, although type I and type III IFN pathways appear to be redundant in cultured cells, in vivo effects are specific to particular anatomic compartments. Therefore, because type I and type III IFNs target different sets of cells within the GI tract, to achieve efficient antiviral protection within the GI tract, particularly against viruses that can replicate in different cell types, co-administration of type I and type III IFNs via a fusion molecule such as the present invention will be particularly effective.

Figure 3:
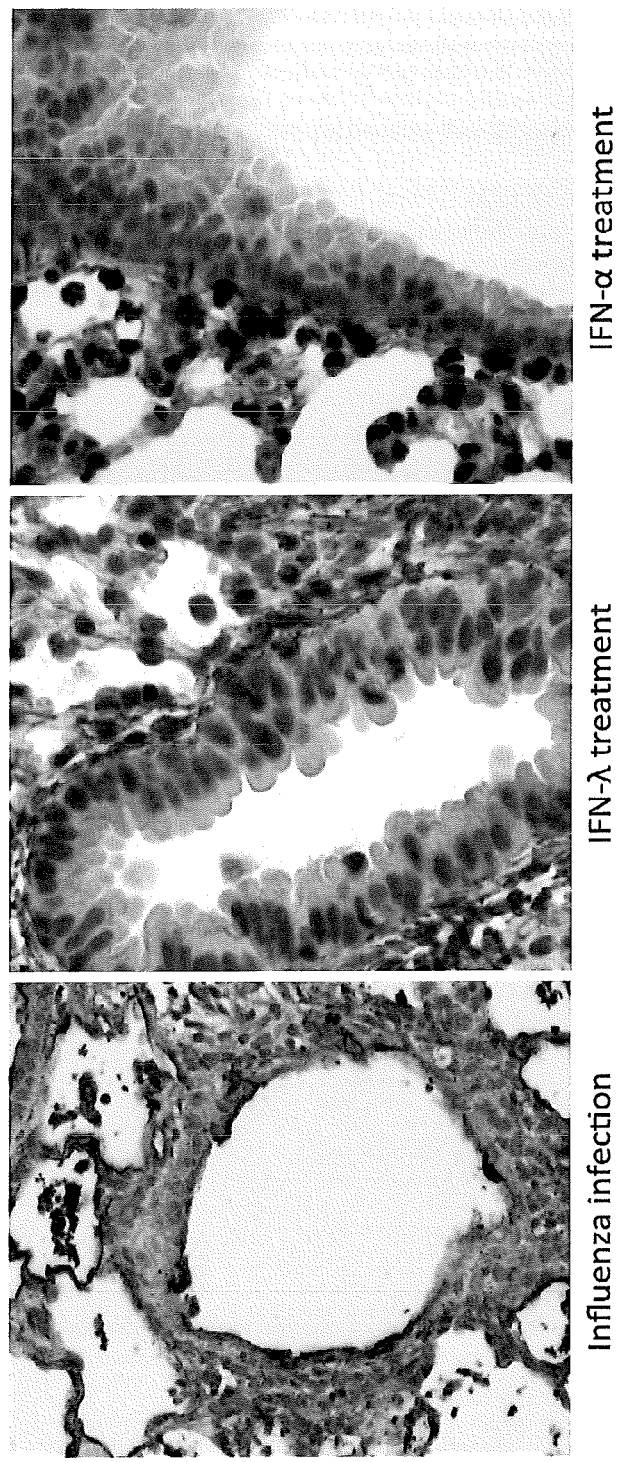
FIGS. 3A, 3B and 3C show IHC staining for viral antigen in airways of IAV-infected mice (FIG. 3A) and IHC staining of pSTAT1 in airways of WT adult mice injected SQ with IFN-α (1 µg.
Figure 4:
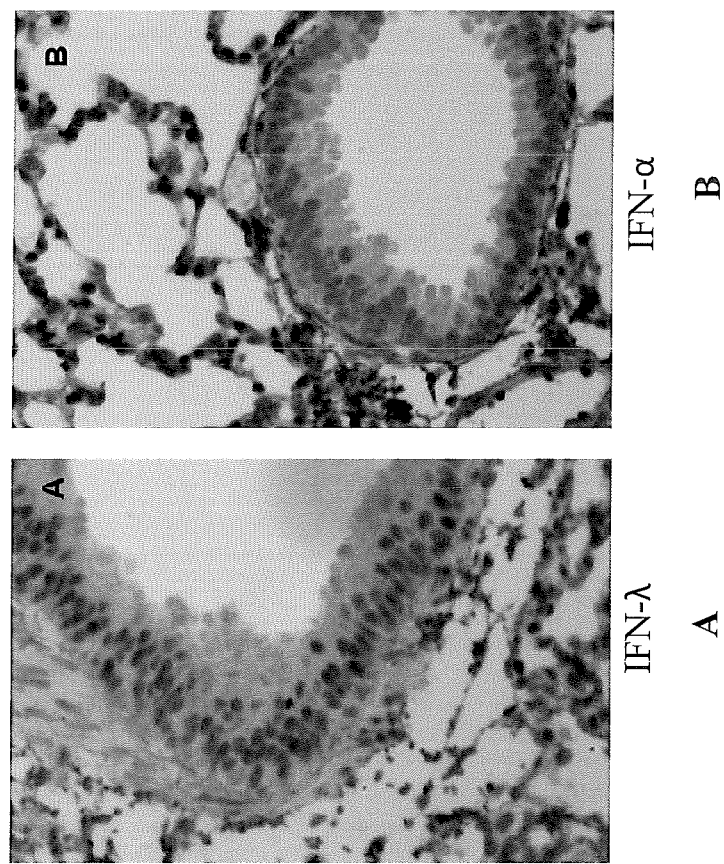
FIGS. 4A and 4B show IHC staining of pSTAT1 in airways of WT adult mice injected intranasally (IN) with IFN-λ (1 µg.
Figure 17:
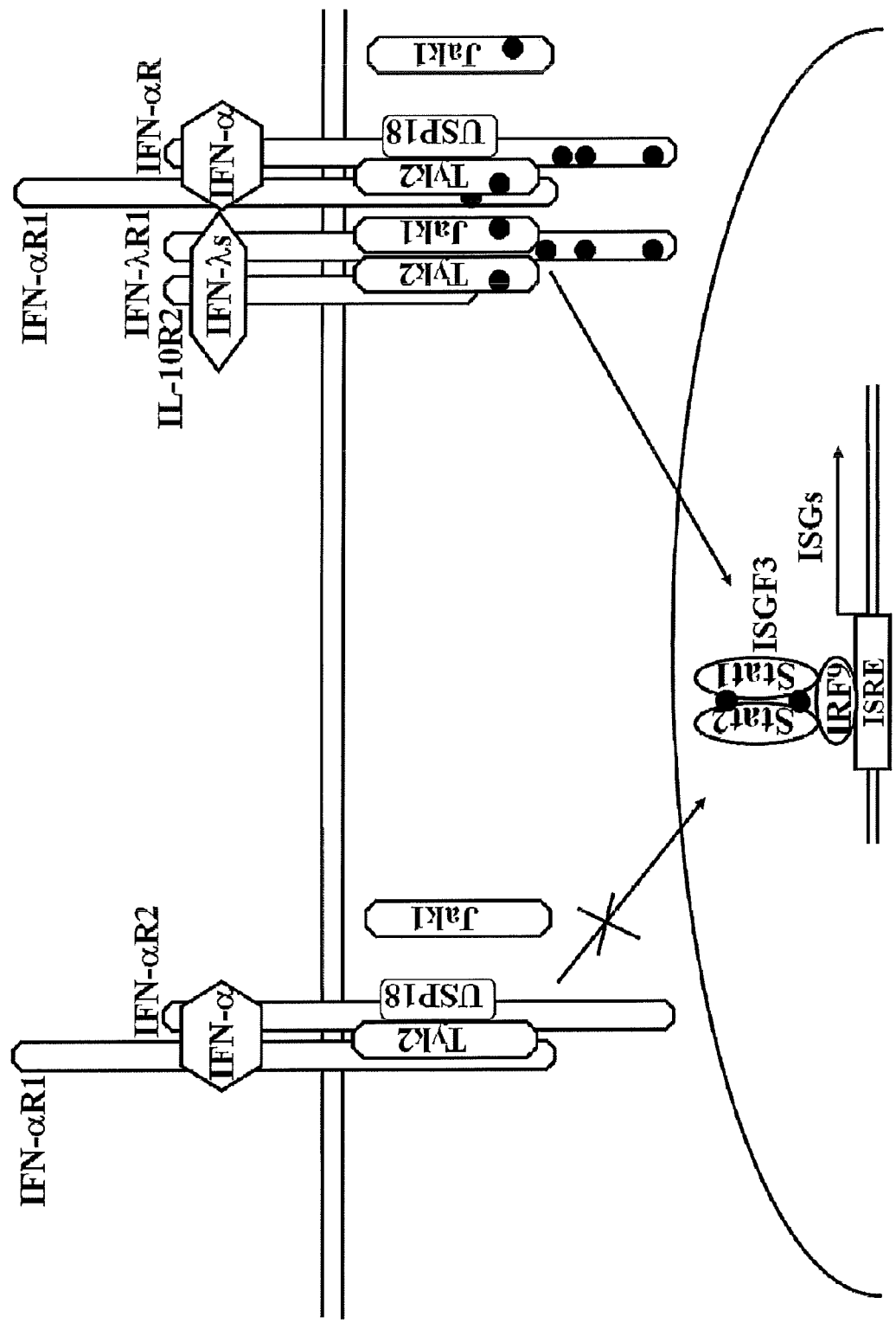
FIG. 17 depicts a model demonstrating the ability of the fusion IFN molecules to signal through a combined type I and type III IFN receptor complex in the presence of a negative regulator USP18. IFN-induced USP18 protein competes with JAK1 for the association with IFN-αR2 and inhibits type I IFN signaling. JAK1 molecule associated with IFN-λR1 supports signaling through both type I and type III IFN receptors within the combined IFN receptor complex that is oligomerized by the IFN fusion molecule.

Similarly, subcutaneous (SQ) administration of IFN-α led to STAT1 activation in alveolar, but not airway (tracheal, bronchial) epithelium, while IFN-λ preferentially acted on the columnar airway-lining cells (see FIGS. 3A-3C). As shown, influenza virus replicates in both cell types (FIGS. 3A-3C). Administration of either IFN-α or IFN-λ by the intranasal injection induced STAT1 phosphorylation and nuclear translocation in a subset of alveoli cells (FIG. 4). However, similar to SQ injection, respiratory epithelial cells lining airways responded only to type III IFN (FIG. 4). These results demonstrate that action of type I and type III IFNs is strictly compartmentalized not only in the GI tract but also in the respiratory tract. Therefore, if type I and type III IFNs do preferentially target different levels of the respiratory tree in vivo, it is expected that the most effective therapeutic approach will involve co-treatment with both IFN types via a fusion molecule such as the present invention to inhibit virus replication in both alveolar and bronchial epithelia. Moreover, it is expected that IFN fusion molecules would induce enhanced IFN signaling in cells expressing all four IFN receptor subunits due to the increased affinity of the fusion IFN molecules in comparison to each IFN acting in combination. In addition, because many viruses down-regulate selected IFN receptor subunits in infected cells or target them for degradation (FIG. 18) to suppress IFN-mediated antiviral responses (Sen, et al. (2017) *J. Virol.* JVI.01394-17), the ability of the IFN fusion molecules to signal trough the remaining type I and type III IFN receptor subunits within the combined type I and type III IFN receptor complex (FIGS. 18 and 19) would still allow the induction of IFN signaling in infected cells. Similarly, type I IFN signaling is quickly down-regulated by the IFN-induced negative regulator USP18, which displaces JAK1 from the association with IFN-αR2 leading to the termination of type I IFN signaling. It is expected that IFN fusion molecules would still be able to engage and activate IFN-αR2 by brining IFN-λR1-associated JAK1 into the tetrameric IFN receptor complex leading to IFN-αR2 phosphorylation and therefore induction of type I IFN signaling in cells expressing USP18 (FIG. 17).

Figure 19:
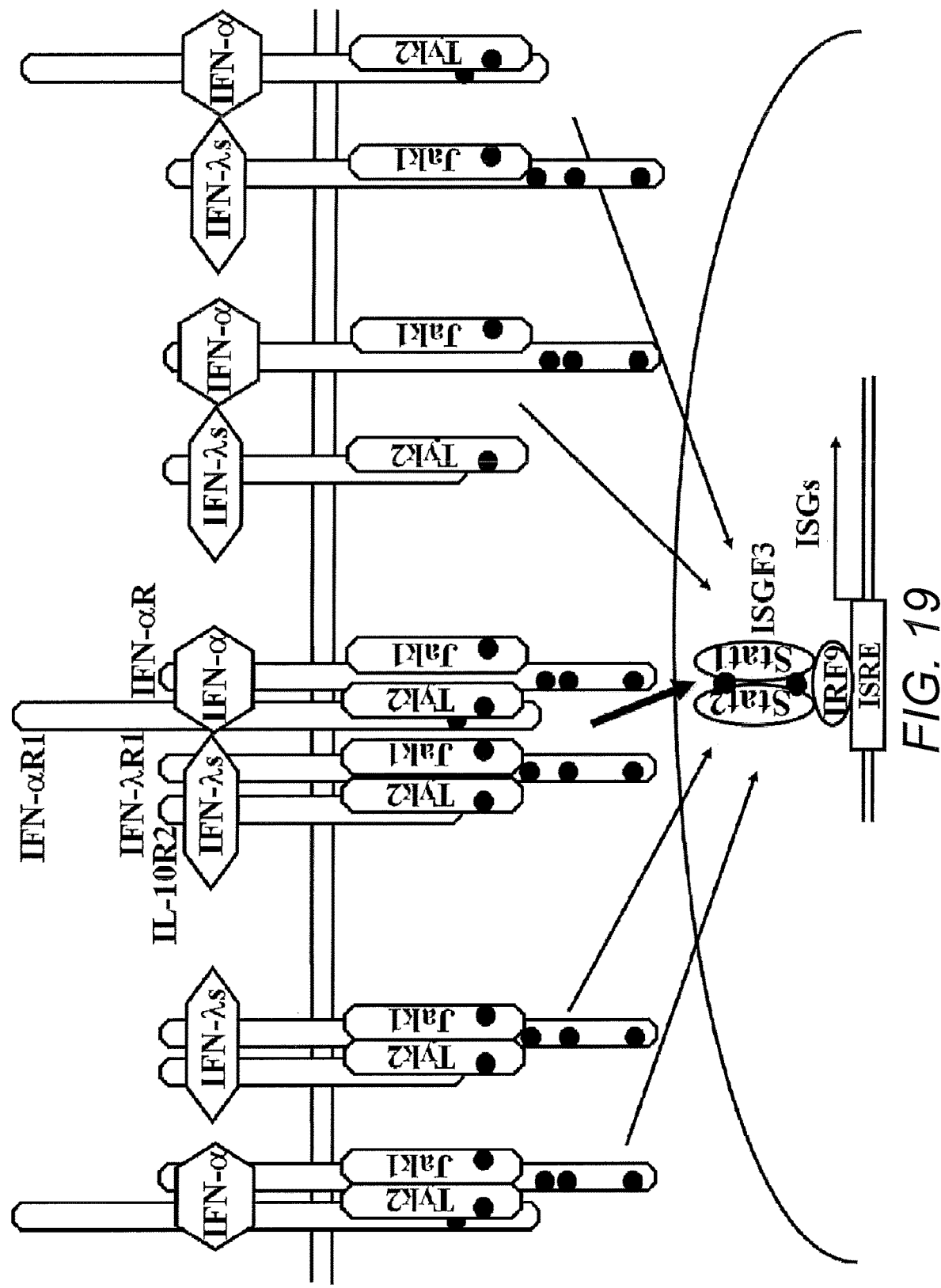
FIG. 19 demonstrates that fusion IFN molecules of the present invention have the ability to induce enhanced signaling through a combined type I and type III IFN receptor complex when all four receptor subunits are present. Also demonstrated herein is the ability of the fusion IFN molecules of the present invention to signal through a combined type I and type III IFN receptor complex when only two (or three) receptor subunits are present. The IFN fusion molecules induce clustering of remaining receptor subunits allowing cross-activation of receptor-associated JAK kinases and induction of IFN signaling cascade.

In addition, various cell types express different levels of specific IFN receptor subunits. For example, intestinal epithelial cells express low levels of IFN-λR2, whereas IFN-λR1 is expressed at higher levels (Mahlakoiv, et al. (2015) PLoS Pathog. 11(4):e1004782). In cells expressing low levels of one or two IFN receptor subunits, IFN fusion molecules would still be able to bind and engage the remaining IFN receptor subunits and induce IFN signaling (FIG. 19).

Figure 5:
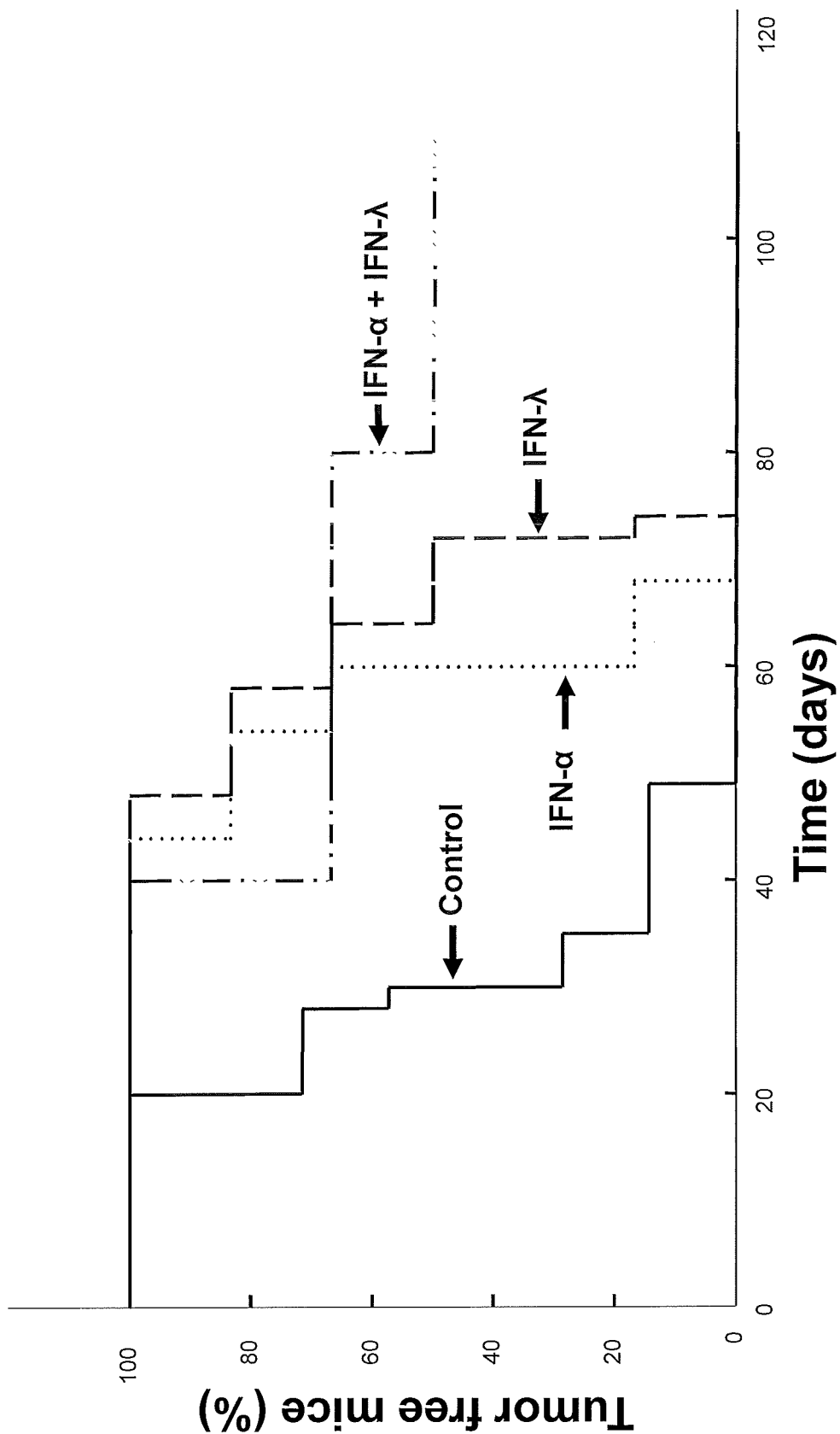
FIG. 5 shows the synergistic effects of IFN-α and IFN-λ on in vivo tumor growth. Mice were injected with parental tumor cells (control) or tumor cells expressing either IFN-α, IFN-λ, or IFN-α+IFN-λ. Tumor survival was monitored and the results show the percent of tumor-free mice.
Figure 6:
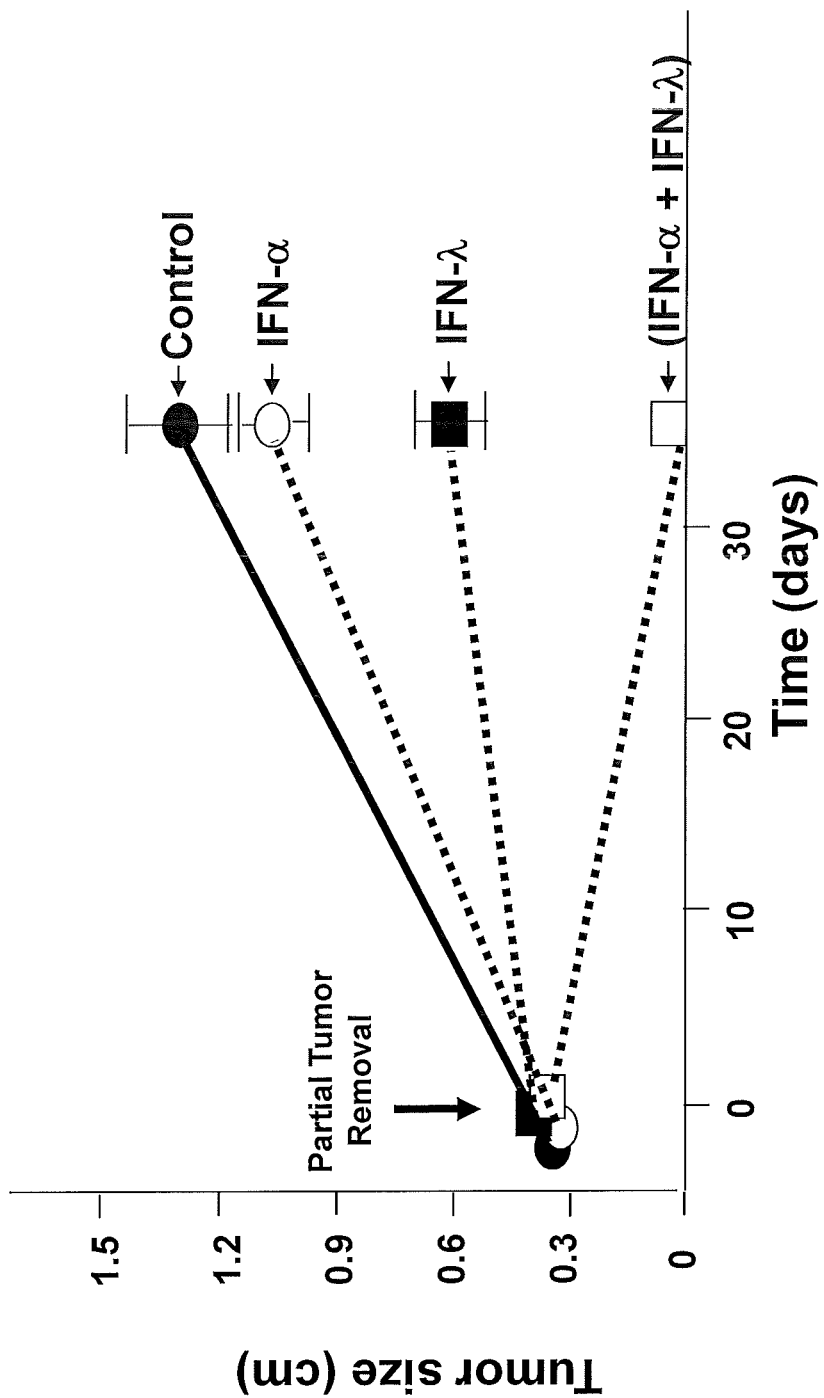
FIG. 6 shows the synergistic effects of IFN-α and IFN-λ on in vivo tumor growth. Mice were injected with $10^6$ parental BNL cells (hepatocellular carcinoma model) and tumors were allowed to form for 4-6 weeks. Approximately 90% of the tumor was surgically removed and mice were subsequently treated with either IFN-α, IFN-λ, or IFN-α+IFN-λ every 2 days for 2 weeks. Tumor size was monitored for 4-6 weeks. Tumor regression or the change in tumor size is shown.
Figure 7:
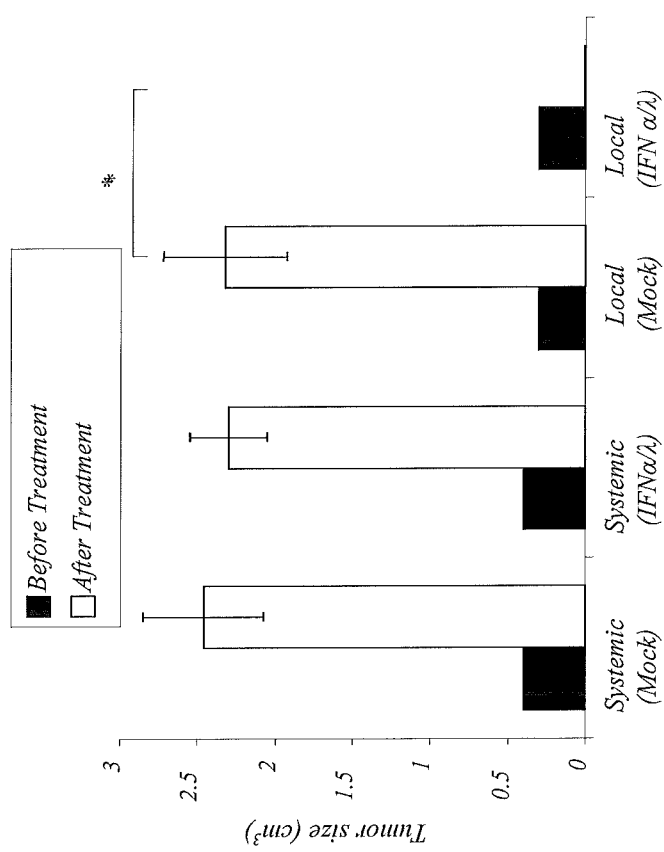
FIG. 7 shows the effect of local and systemic administration of IFN-α+IFN-λ on tumor size as compared to mock administration. The results show that local administration of IFN-α+IFN-λ dramatically reduces tumor size.

Further, each IFN type has unique biological features. For instance, expression of IFN-λ receptors demonstrates a tissue-restricted pattern. Epithelial cells are the main target for type III IFNs. Thus, type III IFNs may be expected to play a critical role in host defense as epithelium is the main barrier for primary viral infections. Many viruses enter the host via the upper alimentary, respiratory, or genitourinary tracts, or damaged skin. Current data demonstrate that type III IFNs are very active on airway and intestinal epithelial cells, and on keratinocytes, suggesting that their antiviral potency will be the strongest in the epithelium-like tissues. Moreover, there is evidence suggesting that polarized epithelial cells of the respiratory tract respond to type I IFNs only at their basolateral and not their apical surface, whereas the cells are still sensitive to type III IFNs at their apical (luminal) side. This unique feature allows IFN-λ-based therapeutics to be effective following intranasal delivery to prevent, inhibit or treat infections with respiratory viruses. Further, since many viruses are able to quickly disseminate into submucosal tissues and infect fibroblast-like cells, type I IFNs are uniquely positioned for protecting submucosal tissues. Intranasal delivery of a type I/type III IFN combination via a fusion molecule of the present invention can provide antiviral protection to uninfected airway epithelial through the action of IFN-λ on the apical surface of intact cells. At the airway sites, where virus infection has already occurred, the integrity of the epithelial barrier can be compromised, and type I IFNs (e.g., co-delivered IFN-α or IFN-β) may gain access to the basolateral surface of epithelial cells as well as to underlying connective tissues, immune cells and endothelial cells within the blood vessels where type III IFNs are not effective (see FIGS. 2-4).

Microarray experiments have demonstrated that type I and type III IFNs induce nearly identical sets of genes. However, similar to in vivo experiments with the Mx2-luciferase reporter mice, kinetics of IFN-stimulated gene expression differ, resulting in a longer-lasting antiviral state in response to type III IFNs, whereas the antiviral state induced by type I IFNs rapidly declines after 24 hours of treatment (see FIG. 10). Therefore, the administration of the IFN fusion molecule will deliver the fast antiviral action of type I IFNs with long lasting antiviral effects of type III IFNs within the same molecule. As discussed supra, the transient action of type I IFNs is mediated by IFN-inducible negative regulator USP18. However the fusion IFN molecule is expected to overcome this negative regulatory mechanism and provide continuous signaling through type I IFN receptor (FIG. 17).

IFN-induced regulatory mechanisms differentially affect type I and type III IFN signaling. For example, an IFN-inducible ISG15 deconjugating ubiquitin protease 43 (UBP43, also known as USP18) has been shown to compete with Jak1 for the binding to the intracellular domain of IFN-αR2 and efficiently suppress IFN-α signaling (FIG. 17; Malakhova, et al. (2006) *EMBO J.* 25:2358-67), whereas USP18 has minimal activity towards the type III IFN receptor. Because of the action of USP18, IFN-treated cells become insensitive to type I IFNs within 6 hours of IFN treatment, with a refractory period lasting up to 72 hours. In contrast, cells respond continuously to type III IFNs. Thus, antiviral resistance can be maintained in cells in the presence of type III IFNs, whereas type I IFNs are faster in triggering initial expression of antiviral mediators in cells.

Infections also target IFN-αR1 or other IFN receptors for degradation or down-regulation thereby inhibiting these type I IFN-mediated biological activities (Sen, et al. (2017) J. Virol. JVI.01394-17). Oligomerization of both type I and type III IFN receptor subunits within one receptor complex triggered by binding of the IFN fusion molecule is expected to result in cross-activation of IFN-αR2-associated JAK1 kinase by kinases associated with IFN-λ receptor subunits allowing signaling though the IFN-αR2 subunit to proceed in the absence of the IFN-αR1 subunit (FIG. 18). Accordingly, the fusion molecules of the present invention are expected to be useful in methods for inducing transcription of IFN-stimulated genes through an IFN-αR2 chain in subjects suffering from an infection which degrades or downregulates an IFN-αR1 chain.

Similarly, the lack of another IFN receptor subunit such as IFN-λR1 or IFN-αR2, or any combination of two receptor subunits due to virus-induced down-regulation or degradation IFN receptor subunits would still allow virus-infected cells to respond to IFN fusion molecules (FIG. 19). Accordingly, the fusion molecules of the present invention are expected to be useful in methods for inducing transcription of IFN-stimulated genes through any two IFN receptor subunits in subjects suffering from an infection which degrades or downregulates one or two IFN receptor chains.

Finally, viruses develop their own IFN-specific countermeasures to circumvent IFN-mediated antiviral protection. For example, some viruses may be more vulnerable to type III IFNs. Several poxviruses, including Variola virus, the causative agent of small pox, encode secreted IFN antagonists that are unable to inhibit type III IFNs (Huang, et al. (2007) *Proc. Natl. Acad. Sci. USA* 104:9822-27). Therefore, type III IFNs may be more effective for the treatment of poxvirus infections.

There is a clear, unmet need for the development of broad-range fast and long acting antivirals, particularly for the purposes of biodefense when the identity of a bioagent is likely to remain unknown for a period of time. In addition, many viruses infect multiple organs and cell types. Therefore, antiviral therapeutics that are capable of eliciting antiviral response on the body-wide level are particularly useful for effective protection against such viruses. A growing body of evidence demonstrates that each type of IFNs has unique functional features, target overlapping but distinct sets of organs and tissues for the induction of antiviral state, and demonstrate different kinetics of their action. Thus, type I and type III IFN antiviral systems have evolved to coordinately induce antiviral defense against specific viral pathogens, and both systems are required for the effective antiviral protection. Therefore, the combination of type I and type III IFNs is required to achieve the maximum levels of antiviral response in multiple organs. Moreover, application of fast-acting IFN-β with slower but longer acting IFN-λ3, IFN-λ1 or IFN-λ2 will provide fast and long lasting maximum level of antiviral protection that is wide-spread and covers the entire organism. The IFN combination therapy of this invention is particularly effective against viruses that are able to replicate in multiple organs or multiple cell types.

In addition, it has now been found that type I and type III IFNs have a synergistic anti-tumor effect in a murine model of cancer (see FIGS. 5 and 6). In one nonlimiting embodiment, local administrations showed a synergistic effect (see FIG. 7). Accordingly, the present invention provides a combination therapy, which includes the coadministration of type I and type III IFNs. In certain embodiments, the type I IFN is IFN-α (e.g., IFN-α2) or IFN-β. In other embodiments, the type III IFN is IFN-λ, in particular IFN-λ1, IFN-λ2 or IFN-λ3.

Figure 20:
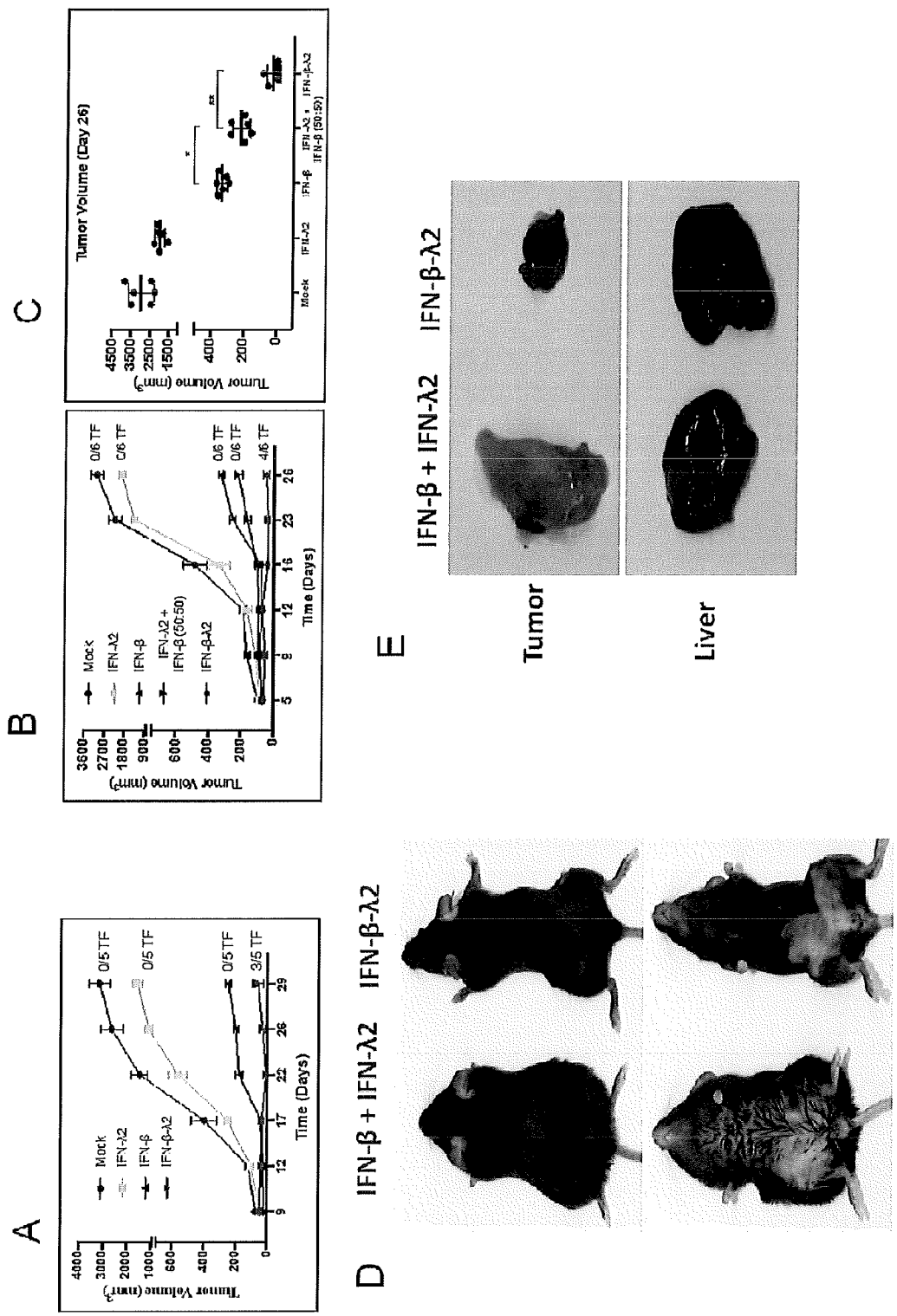
FIGS. 20A, 20B and 20C show suppression of in vivo tumor growth by a fusion IFN molecule IFN-β-IFNλ2. Murine breast cancer E0771 cells were engineered to secrete either murine IFN-λ2, IFN-β or IFN-β-IFNλ2 (IFN-β-λ2) fusion molecule. Tumorigenicity of the modified E0771 cells was assessed in syngeneic C57BL/6 mice. Mice were injected into a mammary fat pad with 0.05 million of the indicated E0771 cells, and tumor development was monitored. Results of two experiments are shown in FIGS. 20A and 20B). Three out of five mice (FIG. 20A) and four out of six mice (FIG. 20B) implanted with E0771 cells expressing fusion IFN-β-λ2 molecule did not develop tumors (TF—tumor free), whereas all mice implanted with E0771 cells expressing single IFN molecules developed tumors.
FIG. 20D shows thickening of the abdominal skin and increased abdominal volume (ascites accumulation) in mice with tumors expressing a combination of single IFN molecules and the lack of these signs in mice with tumors expressing fusion IFN-β-λ2 molecule.
FIG. 20E shows the signs of anemia in tumor and other tissues (liver) in mice with tumors expressing a combination of single IFN molecules and the lack of these signs in mice with tumors expressing fusion IFN-β-λ2 molecule.

Importantly, studies presented in FIG. 20 revealed that the fusion IFN-β-FN-λ2 molecule was much more potent in inhibiting growth of mammary tumor cells than single IFN molecules and more potent than a combination of IFN-β and IFN-λ2. Four out of six mice implanted with mammary tumor cells expressing the fusion IFN-β-FN-λ2 protein remained tumor free, whereas all mice injected with the mixture of tumor cells expressing either IFN-β or FN-λ2 developed tumors. The IFN-β-FN-λ2 expressing tumors, which developed in two mice, were smaller in size than tumors in mice implanted with the mixture of tumor cells expressing either IFN-β or FN-λ2. Therefore, the IFN fusion molecule exhibited enhanced synergistic anti-tumor activities as compared to the combination type I and type III IFN therapy. Moreover, increased abdominal volume (ascites accumulation) as well as signs of severe anemia in tumor and other tissues (liver) were observed in mice with tumors expressing a combination of single IFN molecules. Similar symptoms and signs were not observed in mice with tumors expressing fusion IFN-β-λ2 molecule (FIGS. 20D and 20E). Anemia is a known side effect of type I IFN therapy due to type I IFN induced suppression of hematopoiesis and angiostatic effects. The lack of these side effects in mice with tumors expressing an IFN fusion molecule of the present invention is indicative of a safer profile for the fusion molecule because the fusion molecule may lack or impose milder side effects in comparison to type I IFN therapy or even to the combination IFN type I and type III therapy. In addition, these data demonstrate that the IFN fusion molecule has unique biological activities and profile, which are distinct from those of the mixture of type I and type III IFNs.

Figure 8:
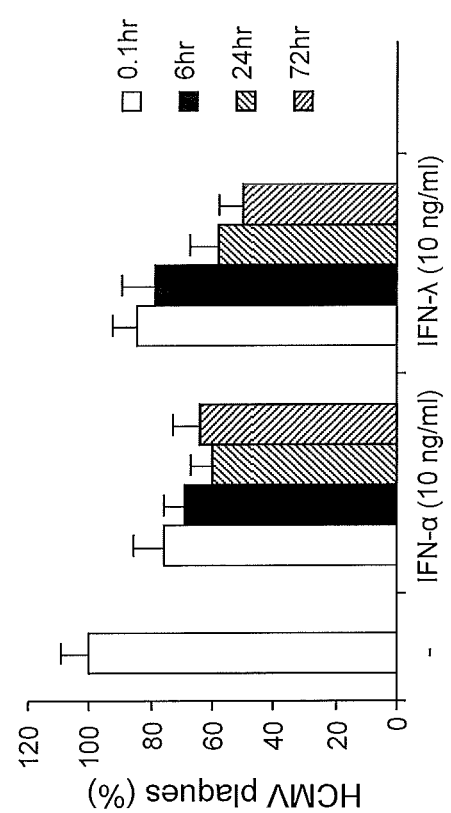
FIG. 8 shows that IFN-α and IFN-λ induce protection against human cytomegalovirus (HCMV) in ARPE-19 cells, a human retinal pigment epithelial cell line, when cells were pretreated with IFNs 0.1, 6, 24 and 72 hours prior to HCMV infection.
Figure 9:
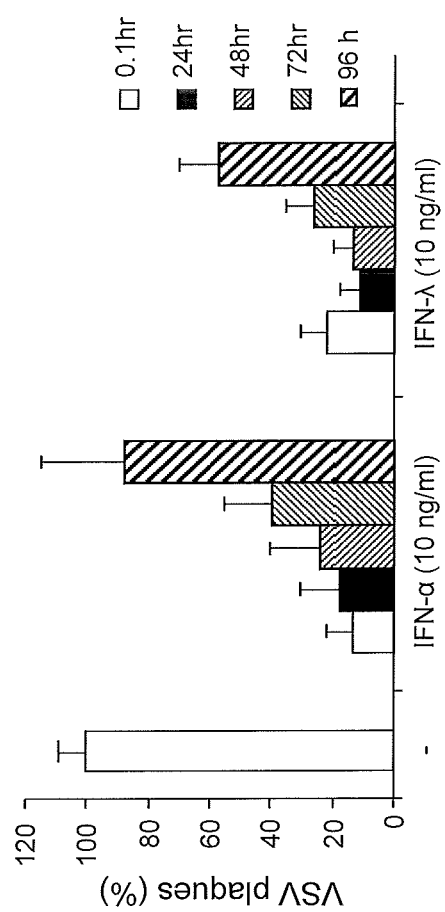
FIG. 9 shows that IFN-α and IFN-λ induce protection against vesicular stomatitis virus (VSV) in ARPE-19 cells, when cells were pretreated with IFNs 0.1, 6, 24, 72 and 96 hours prior to VSV infection.
Figure 10:
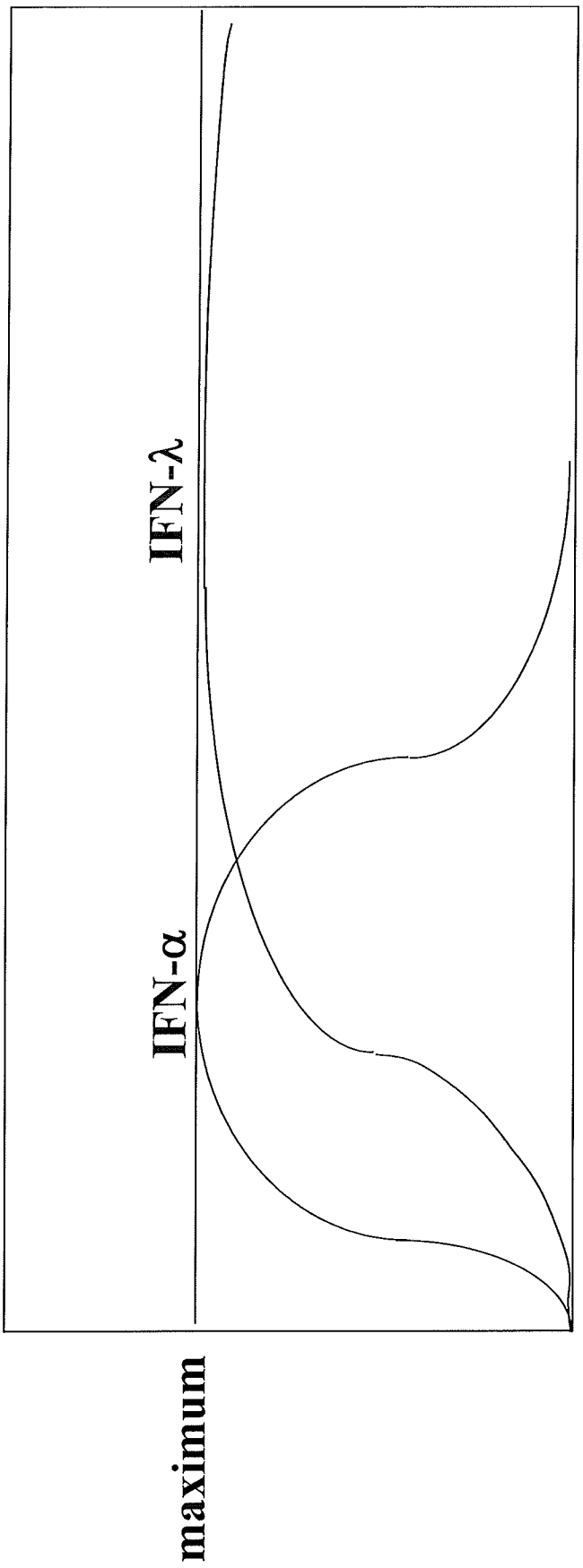
FIG. 10 illustrates differential kinetics of antiviral response induced by type I and type III IFNs. As such the combined use of type I and type III IFNs provides a fast, long-lasting, efficient, and widespread antiviral response.
Figure 11:
FIG. 11 shows a schematic of the structure of the human type I IFN (IFN-I) and type III IFN (IFN-III) fusion molecule with the signal peptide (SP) derived from type I IFN. A linker sequence is depicted between two IFN proteins.
Figure 15:
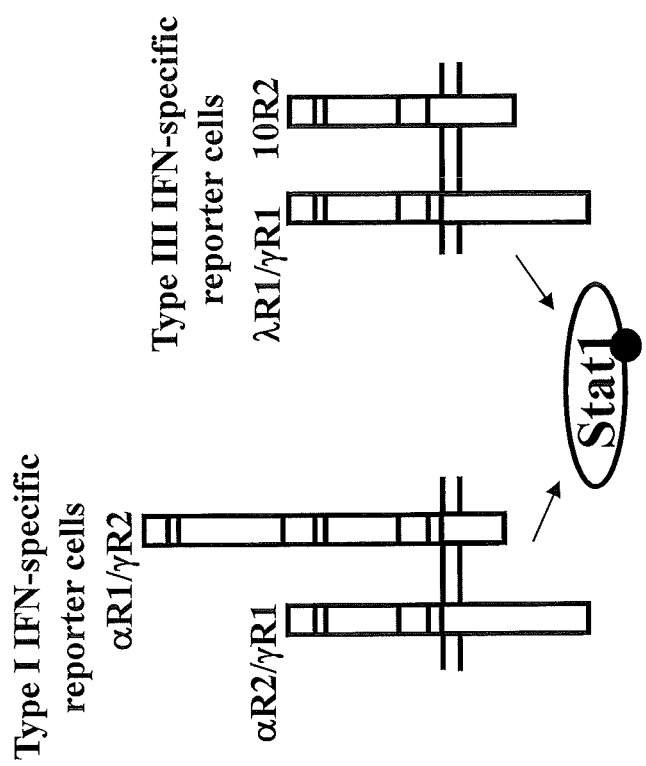
FIG. 15 provides a schematic of reporter CHO cell lines expressing chimeric receptor complexes for either human type I or type III IFNs.
Figure 16:
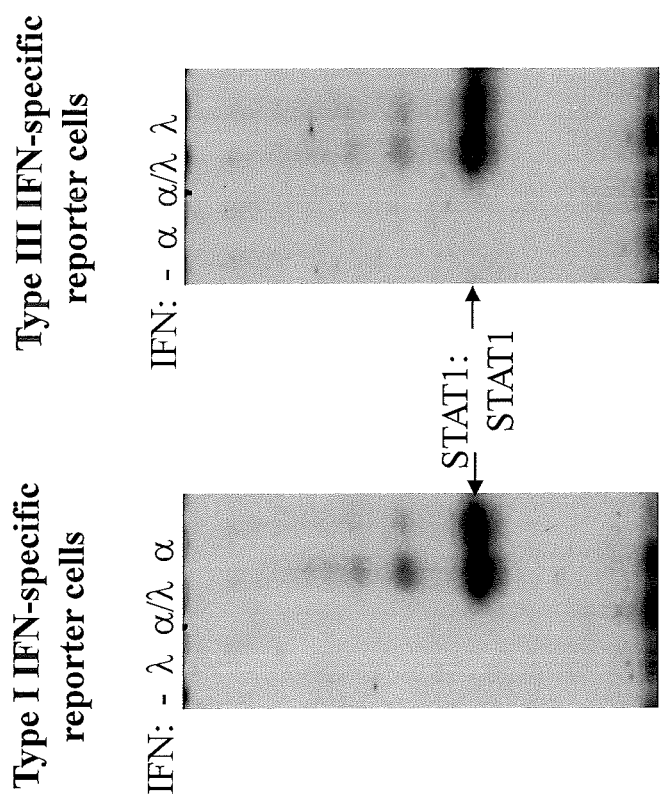
FIG. 16 shows that treatment of reporter CHO cell lines with the fusion IFN protein of the invention (10 ng/ml) results in STAT1 activation as determined by electrophoretic mobility shift assay (EMSA).

Given that treatment of mice with either IFN-α or IFN-λ alone leads to the activation of antiviral responses (see FIGS. 8 and 9), in particular in overlapping but distinct organs, tissues and cell types, simultaneous administration of type I and type III IFNs is expected to provide a long-lasting, efficient, and widespread antiviral response (FIG. 10). Therefore, the combination of type I and type III IFNs is also of use in the prevention and/or treatment of viral infection. To facilitate the co-delivery of type I and type III IFNs, one nonlimiting embodiment of the present invention provides an IFN-α or IFN-β and IFN-λ fusion molecule (see e.g. FIGS. 11-14 and 21-22). This fusion molecule retains functional activities of both type I and type III IFNs as demonstrated by the ability of the IFN-α2 and IFN-λ1 fusion molecule to trigger activation of STAT1 in reporter cell lines that are responsive to either type I or type III IFNs (FIGS. 15 and 16). In this assay, STAT1 activation was assessed in the reporter cell lines, in which intracellular signaling is mediated by the intracellular domain(s) of IFN-γ receptor and did not involve tetramerization of type I and type III IFN receptor subunits by the IFN fusion molecule, which is expected to occur in normal human cells (FIG. 19). STAT1 activation was measured in EMSA that evaluates IFN-induced dimerization of STAT1 and binding of STAT1 dimers to the radioactively labeled DNA probe. Formation of STAT1 dimers requires phosphorylation of STAT1 on Tyr701. Although Tyr phosphorylation of STAT1 and STAT2 leading to the formation of the ISGF3 transcription complex is a hallmark a unique feature of both type I and type III IFN-induced JAK-STAT signaling cascades, several additional post-translational modifications, including methylation, acetylation, Ser phosphorylation, etc., have been reported and can affect kinetics and magnitude of ISG expression, as well as preferential selectivity for specific subsets of ISGs. The ISGF3 complex is clearly activated by the IFN fusion molecules, because the fusion molecule induced antiviral protection (FIG. 24), which is dependent on ISGF3 activation. However, because it is likely that some of the secondary post-translational modification within the ISGF3 may differ between type I and type III IFN signaling, it is expected that ISGF3 activated in response to the fusion molecule may not be identical to ISGF3 induced in response to single IFN molecules and may therefore trigger an altered profile of ISG expression in terms of kinetics, magnitude or ISG subset selectivity.

There are particular advantages of using the IFN fusion molecule over a combination of separate IFN proteins.

For example, the fusion molecule provides for simplified production of the therapeutic agent and delivery of a single therapeutic agent.

Further, as discussed above, studies with the use of Mx2 luciferase reporter mice demonstrated that type I IFNs preferentially target liver, whereas type III IFNs are uniquely active in GI tract and airway epithelium. Nevertheless, various human hepatocyte-like cell lines as well as cell lines derived from GI and respiratory tracts are responsive to both type I and type III IFNs. Moreover, freshly isolated murine hepatocytes as well as intestinal epithelial cells are responsive to both types of IFNs. Therefore, the lack or weak responsiveness of selected organs and tissues to specific IFNs in vivo may be a result of differential deliverability of type I and type III IFNs. Thus, a fusion molecule would deliver both IFN-α and IFN-β to all tissues and organs.

In addition, since type I and type III IFNs target distinct, only partially overlapping cell types, administration of type I and type III IFNs as a fusion molecule provides for action on a wider variety of cells. Further, in cells responding to both types of IFNs, there is a cross-regulation of signaling between type I and type III IFNs; for example, action of both types of IFNs is required to render neutrophils fully functional in controlling invasive fungal growth (Espinosa, et al., (2017) *Sci. Immunol.* (16) pii: eaan5357). Accordingly, administration of type I and type III IFNs as a fusion molecule would be useful in this application as well.

As discussed supra, IFN fusion molecules are expected to overcome negative regulatory effects of IFN-inducible USP18 protein, allowing prolonged signaling through the type I IFN pathway. Although expression of IFN-AR1 is limited to specific cell types, IL-10R2 is ubiquitously expressed. Therefore, the fusion molecule will engage three receptor subunits in type I IFN responsive cells. This receptor should have higher affinity enabling stronger signaling through these trimeric IFN receptor complexes than signaling through the heterodimeric type I IFN receptor complex. Similarly, a variety of epithelial cells that primarily respond only to type III IFNs still express lower levels of one or both type I IFN receptor subunits. Therefore, the IFN fusion molecule would engage expression in the lower level type I IFN receptor subunit(s) resulting in some complexes being composed of three or four IFN receptor subunits. These complexes would be high affinity receptor complexes and lead to stronger IFN signaling in epithelial cells.

Furthermore, the fusion molecule is of use for intranasal delivery. As discussed supra, apical surface of airway epithelial cells responds primarily to type III IFNs. Therefore, intranasal delivery of a type I and type III IFN fusion molecule provides antiviral protection to uninfected airway epithelial cells though the action of IFN-λ on the apical surface of intact cells. The type I IFN part of the IFN fusion molecule can gain access to the basolateral surface of the top layer of airway lining epithelial cells as well as to underlying connective tissues when the apical IFN-λ receptor complex is internalized after binding the IFN fusion molecule and then recycled together with the fusion molecule to the basolateral surface of epithelial cells.

Figure 18:
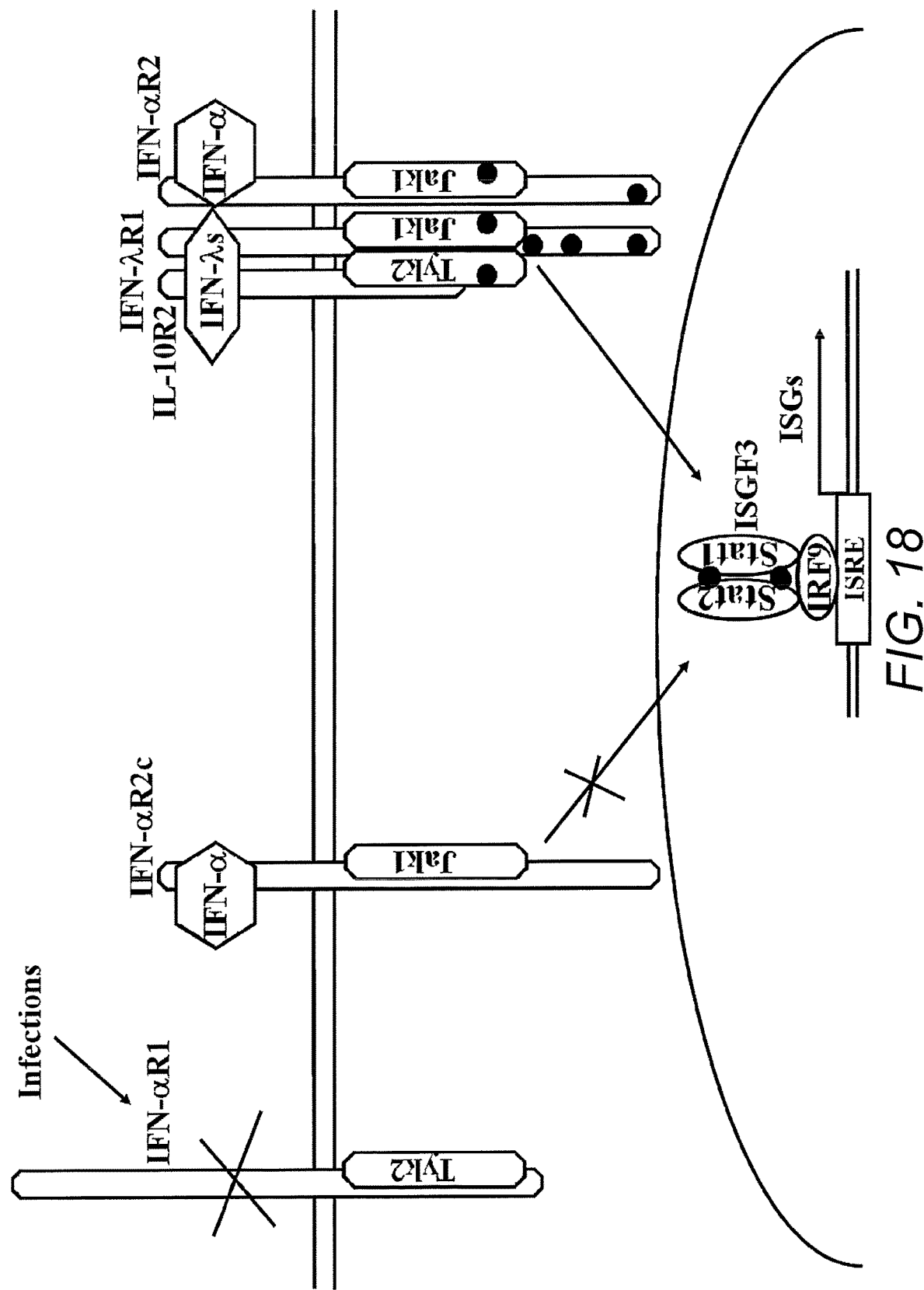
FIG. 18 depicts a model demonstrating the ability of the fusion IFN molecules to signal through a combined type I and type III IFN receptor complex in the absence of the IFN-αR1 chain. Infections target the IFN-αR1 chain for down-regulation and degradation to inhibit type I IFN signaling. The IFN fusion molecules induce clustering of remaining receptor subunits allowing cross-activation of receptor-associated JAK kinases and induction of IFN signaling cascade.

Moreover, the fusion molecule will have higher efficacy due to higher affinity binding to the receptors. It is expected that the fusion molecule will induce the oligomerization of the type I and type III IFN receptor complexes resulting in the increased affinity of the fusion molecule to the combined cell surface receptor complex and translate into stronger antiviral activity (FIG. 19). In other words, the fusion IFN molecule binds to the tetrameric receptor complex, whereas single IFN molecules bind to homodimeric receptor complexes (FIG. 19). Therefore, it is expected that the fusion molecules should have higher affinity for the receptor than single IFN molecules. In addition, since USP18 expels Jak1 only from the type I receptor complex, the combined type I and type III IFN receptor complex that is brought together by the IFN fusion molecule (FIG. 17) will still have Jak1 associated with the IFN-λ receptor. This Jak1 can phosphorylate (activate) intracellular domains of both IFN-λR1 and IFN-αR2 chains thereby allowing signaling through both type I and type III IFN receptors to proceed normally even in the presence of negative regulator USP18. Similarly, the IFN fusion molecule should be able to induce signaling through the IFN-αR2 chain in the case when the IFN-αR1 chain is down-regulated by infection (FIG. 18). Other negative regulators, like SOCS1 and SOCS3 also show preferential inhibition of type I vs type III IFN signaling pathways. Since the fusion molecule binds and clusters four receptor subunits at the same time, the lack of one or even two receptor subunits, due to proteosomal degradation or due to the action of inhibitory molecules, should not block the ability of the fusion IFN molecules to signal through the remaining 2 or 3 receptor subunits. In other words, the presence of either two out of four receptor subunits should be sufficient for the fusion molecules to induce downstream signaling cascade and biological activities, whereas removal or blocking of just one receptor subunit in either type I or type III IFN receptor complex, leads to complete inhibition of signaling by single IFN molecules. The increased affinity of the fusion molecules for the tetrameric receptor complex, as well as the lower sensitivity to the inhibitory signal should render IFN fusion molecules more biologically potent than the IFN combination. It is also likely that IFN receptor subunits within the tetrameric complex have different affinities for shared downstream signaling participants such as JAK kinases and STATs, and would compete for the limited amount of these signaling molecules. Therefore, signaling within the tetrameric IFN receptor complex may be shunted toward one of the IFN type-specific signaling pathways. In addition, IFN-λ signaling appear to engage JAK2 tyrosine kinase during signal transduction events (Lee, et al. (2012) Int. J. Mol. Med. 30:945-952). The fusion molecule would therefore bring JAK2 kinase into the combined IFN receptor complex and may modulate type I IFN signaling. There are also reports that type III IFNs reduce permeability of the blood-brain barrier independently of STAT1 activation (Lazear, et al. (2015) Sci. Transl. Med. 7:284ra259). Therefore, the fusion IFN molecule is expected to engage pathways complimentary or additional to the canonical JAK-STAT signaling. As discussed supra, post-translational modification of the ISGF3 transcriptional complex in addition to canonical Tyr phosphorylation of STAT1 and STAT2 may be also different in response to IFN fusion molecules versus single IFNs, which may affect kinetics, magnitude and subset selectivity of ISG expression and subsequent biological activities. Dys-regulated or over-exacerbated type I IFN activities have been associated with auto-immune conditions such as lupus as well as chronic viral infections. In addition to a subset of antiviral ISGs that is induced by both type I and type III IFNs, type I but not type III IFNs also induce a set of ISGs encoding pro-inflammatory mediators (Galani, et al. (2017) Immunity 46(5):875-890.e6). As discussed supra, subtle changes in post-translational modifications of ISGF3 in response to IFN fusion molecules could eliminate or reduce expression of this set of pro-inflammatory ISGs in response to fusion molecules. Moreover, type III IFNs were reported to stimulate development and proliferation of immunosuppressive T regulatory cells through their action on dendritic cells (Mennechet, et al. (2006) Blood 107(11):4417-23). Dendritic cells respond to both types of IFNs, and type I IFNs exert immune-stimulatory activities on these cells. Therefore, IFN fusion molecules are expected to alter responsiveness of dendritic cells to IFNs and may elicit a more balanced and better-tuned activation of the cells avoiding their over-activation by type I IFNs.

As indicated, the present invention includes a fusion molecule composed of a type I IFN protein or portion thereof and type III IFN protein or portion thereof. The fusion molecule can have either the type I or type III at the N-terminus, i.e., a type I-type III fusion or type III-type I fusion. Nonlimiting exemplary fusion molecules are depicted in FIGS. 12-14 and FIGS. 21-22. The fusion molecule may or may not include a signal peptide at its N-terminus. As is known in the art, a "signal peptide" is a peptide usually present at the N-terminal end of newly synthesized secretory or membrane proteins, which directs the proteins across or into a cell membrane of the cell (the plasma membrane in prokaryotes and the endoplasmic reticulum membrane in eukaryotes). It is usually subsequently removed. When a signal peptide is included, the signal peptide can originate from either the type I or type III IFN protein, or can be obtained from any known protein known to be secreted. Nonlimiting exemplary signal peptide sequences are listed in Table 1. In some embodiments, the fusion molecule of this invention has an N-terminal signal peptide. In particular embodiments, the signal peptide is set forth in SEQ ID NO:1.

TABLE 1

| Signal Peptide Sequence | SEQ ID NO: |
| --- | --- |
| MALTFALLVALLVLS[1] | 1 |
| MAAAWTVVLVTLVLGLAVAGPV[2] | 2 |
| MTGDCTPVLVLMAAVLTVTGAV[3] | 3 |
| MTGDCMPVLVLMAAVLTVTGAV[4] | 4 |
| MTNKCLLQIALLLCFSTTALS[5] | 5 |
| MLKRSSWLATLGLLTVASVSTIVYA[6] | 6 |
| MKKATFITCLLAVLLVSNPIWNA[6] | 7 |
| MKVSAAALAVILIATALCAPASA[6] | 8 |

TABLE 1-continued

| Signal Peptide Sequence | SEQ ID NO: |
|---|---|
| MKVSTAFLCLLLTVSAFSAQVLA[6] | 9 |
| MKCLLLALGLALACAAQA[6] | 10 |
| MARLCAFLMTLLVMSYWSTCSLG[7] | 11 |
| MNNRWILHAAFLLCFSTTALS[8] | 12 |

[1]Human IFN-α2a; [2]Human IFN-λ1; [3]Human IFN-λ2; [4]Human IFN-λ3; [5]Human IFN-β; [6]Signal peptide for secretion of recombinant proteins by host cells, see WO 2009/147382; [7]Mouse IFN-α; [8]Mouse IFN-β.

Type I IFN proteins for use in the fusion molecule of the invention include but are not limited to IFN-α (alpha), IFN-β (beta), IFN-κ (kappa), IFN-ε (epsilon), and IFN-ω (omega) or portions thereof. The genetics and structure of these proteins are well-known in the art and described by, e.g., Samarajiwa, et al. (2006) *The Interferons: Characterization and Application,* Wiley-VCH, pages 3-34. In some embodiments, the type I IFN is a mammalian type I IFN. In certain embodiments, the type I IFN is a human type I IFN. In particular embodiments, the type I IFN is an IFN-α protein (e.g., IFN-α2) or IFN-β protein (e.g., IFN-β1) or portion thereof. IFN-β proteins are produced in large quantities by fibroblasts and are known to exhibit antiviral activity. Two types of IFN-β have been described, IFN-β1 (IFNB1) and IFN-β3 (IFNB3). The IFN-α proteins are produced by leukocytes. They are mainly involved in innate immune response against viral infection and include 13 subtypes: IFNA1 (GENBANK Accession No. BAM72353), IFNA2 (GENBANK Accession No. NP 000596), IFNA4 (GENBANK Accession No. NP_066546), IFNA5 (GENBANK Accession No. NP_002160), IFNA6 (GENBANK Accession No. NP_066282), IFNA7 (GENBANK Accession No. NP_066401), IFNA8 (GENBANK Accession No. NP 002161), IFNA10 (GENBANK Accession No. NP_002162), IFNA13 (GENBANK Accession No. AAH69427), IFNA14 (GENBANK Accession No. AAI04160), IFNA16 (GENBANK Accession No. NP_002164), IFNA17 (GENBANK Accession No. NP_067091), and IFNA21 (GENBANK Accession No. NP_002166). Human type I IFN proteins also include IFN-ω (GENBANK Accession No. NP_002168), IFN-κ (GENBANK Accession No. NP_064509) IFN-ε (GENBANK Accession No. NP_795372). The genes encoding type I IFN proteins are found together in a cluster on chromosome 9. Specific examples of commercially available IFN products include IFN-γ1b (ACTIMMUNE®), IFN-β1a (AVONEX®, and REBIF®), IFN-β1b (BETASERON®), IFN alfacon-1 (INFERGEN®), IFN-α2 (INTRON A®), IFN-α2a (ROFERON-A®), Peginterferon alfa-2a (PEGASYS®), and Peginterferon alfa-2b (PEG-INTRON®), each of which find use in this invention. Nonlimiting exemplary mature type I IFN proteins are listed in Table 2.

TABLE 2

| Type I IFN sequence | SEQ ID NO: |
|---|---|
| CKSSCSVGCDLPQTHSLGSRRTLMLLAQMRRISLFSCLKDRH DFGFPQEEFGNQFQKAETIPVLHEMIQQIFNLFSTKDSSAAW DETLLDKFYTELYQQLNDLEACVIQGVGVTETPLMKEDSILA VRKYFQRITLYLKEKKYSPCAWEVVRAEIMRSFSLSTNLQES LRSKE[1] | 13 |

TABLE 2-continued

| Type I IFN sequence | SEQ ID NO: |
|---|---|
| CKSSCSVGCDLPQTHSLGSRRTLMLLAQMRRISLFSCLKDRH DFGFPQEEFGNQFQKAETIPVLHEMIQLIFNLFSTKDSSAAW DETLLDKFYTELYQQLNDLEACVIQGVGVTETPLMKEDSILA VRKYFQRITLYLKEKKYSPCAWEVVRAEIMRSFSLSTNLQES LRSKE[2] | 14 |
| MSYNLLGFLQRSSNFQCQKLLWQLNGRLEYCLKDRMNFDIPE EIKQLQQFQKEDAALTIYEMLQNIFAIFRQDSSSTGWNETIV ENLLANVYHQINHLKTVLEEKLEKEDFTRGKLMSSLHLKRYY GRILHYLKAKEYSHCAWTIVRVEILRNFYFINRLTGYLRN[3] | 15 |

[1]Human IFN-α2a; [2]Human IFN-α2b; [3]Human IFN-β.

Type III IFN proteins are also known in the art and described in U.S. Pat. No. 7,820,793, incorporated herein by reference in its entirety. Type III IFNs include IFN-λ1, IFN-λ2 and IFN-λ3 (also called IL29, IL28A and IL28B, respectively) and portions thereof. These IFNs signal through a receptor complex composed of IL10R2 (also called CRF2-4) and IFNLR1 (also called CRF2-12). In one embodiment, the type III IFN is a mammalian type III IFN. In another embodiment, the type III IFN is a human type III IFN. In some embodiments, the type III IFN is IFN-λ1 (GENBANK Accession No. NP_742152 and 3OG6_A), IFN-λ2 (GENBANK Accession No. NP_742150 and AAN86126), or IFN-λ3 (GENBANK Accession No. NP_742151 and AAN86127). Exemplary mature IFN-λ proteins are listed in Table 3. In particular embodiments, the type III IFN is IFN-λ1. Some of the type I IFN proteins such as IFN-β, IFN-ε, IFN-κ and type III IFN proteins such as IFN-λ1, IFN-λ-2 and IFN-λ3 have unpaired Cys residues that can be substituted to improve folding and purification of the fusion molecules. Variants of type I and type III IFNs with lower affinity to their corresponding receptors can be also used for the generation of the fusion IFN proteins to reduce their signaling capabilities though their individual heterodimeric IFN receptor complexes, but preserve their synergistic activities though the combined tetrameric IFN receptor complex. Nonlimiting exemplary type III IFN sequence are set forth in Table 3.

TABLE 3

| Type III IFN sequence | SEQ ID NO: |
|---|---|
| PVPTSKPTPTGKGCHIGRFKSLSPQELASFKKARDALEESLK LKNWSCSSPVFPGNWDLRLLQVRERPVALEAELALTLKVLEA AAGPALEDVLDQPLHTLHHILSQLQACIQPQPTAGPRPRGRL HHWLHRLQEAPKKESAGCLEASVTFNLFRLLTRDLKYVADGN LCLRTSTHPEST[1] | 16 |
| PVPTSKPTTTGKGCHIGRFKSLSPQELASFKKARDALEESLK LKNWSCSSPVFPGNWDLRLLQVRERPVALEAELALTLKVLEA AAGPALEDVLDQPLHTLHHILSQLQACIQPQPTAGPRPRGRL HHWLHRLQEAPKKESAGCLEASVTFNLFRLLTRDLKYVADGN LCLRTSTHPEST[2] | 17 |
| PVARLHGALPDARGCHIAQFKSLSPQELQAFKRAKDALEESL LLKDCRCHSRLFPRTWDLRQLQVRERPMALEAELALTLKVLE ATADTDPALVDVLDQPLHTLHHILSQFRACIQPQPTAGPRTR GRLHHWLYRLQEAPKKESPGCLEASVTFNLFRLLTRDLNCVA SGDLCV[3] | 18 |
| PVARLHGALPDARGCHIAQFKSLSPQELQAFKRAKDALEESL LLKDCRCHSRLFPRTWDLRQLQVRERPMALEAELALTLKVLE ATADTDPALVDVLDQPLHTLHHILSQFRACIQPQPTAGPRAR GRLHHWLYRLQEAPKKESPGCLEASVTFNLFRLLTRDLNCVA SGDLCV[4] | 19 |

TABLE 3-continued

| Type III IFN sequence | SEQ ID NO: |
|---|---|
| PVARLRGALPDARGCHIAQFKSLSPQELQAFKRAKDALEESL LLKDCKCRSRLFPRTWDLRQLQVRERPVALEAELALTLKVLE ASADTDPALGDVLDQPLHTLHHILSQLRACIQPQPTAGPRTR GRLHHWLYRLQEAPKKESPGCLEASVTFNLFRLLTRDLNCVA SGDLCV[5] | 20 |
| PVARLRGALPDARGCHIAQFKSLSPQELQAFKRAKDALEESL LLKDCKCRSRLFPRTWDLRQLQVRERPVALEAELALTLKVLE ATADTDPALGDVLDQPLHTLHHILSQLRACIQPQPTAGPRTR GRLHHWLHRLQEAPKKESPGCLEASVTFNLFRLLTRDLNCVA SGDLCV[6] | 21 |
| PRRCLLSHYRSLEPRTLAAAKALRDRYEEEALSWGQRNCSFR PRRDPPRPSSCARLRHVARGIADAQAVLSGLHRSELLPGAGP ILELLAAAGRDVAACLELARPGSSRKVPGAQKRRHKPRRADS PRCRKASVVFNLLRLLTWELR LAAHSGPCL[7] | 22 |

[1,2]Human IFN-λ1; [3,4]Human IFN-λ2; [5,6]Human IFN-λ2; [7]Human IFN-λ4.

While the type I IFN and type III IFN proteins or portions thereof may be directly attached to each other, in some embodiments, the type I IFN and type III IFN proteins or portions thereof are joined to one another by a linker. In this respect, the fusion molecule of the invention can have the structure (N→C terminal orientation) of Type I IFN-Linker-Type III IFN or Type III IFN-Linker-Type I IFN. Linkers of use in the instant fusion molecule are preferably flexible and have a length in the range of 5-50 amino acids, or more preferably 10-30 amino acids. In certain embodiments, the linker element is a glycine/serine linker, i.e. a peptide linker substantially composed of the amino acids glycine and serine. Amino acids threonine or alanine can be also used within the linker. It will be clear to the skilled person that in cases in which the IFN on the N-terminal end of the fusion molecule already terminates with, e.g., a Gly, such a Gly may form the first Gly of the linker in the linker sequence. Likewise, in cases in which the C-terminal IFN begins with, e.g., a Pro, such a Pro residue may form the last Pro of the linker in the linker sequence. Nonlimiting examples of specific linker sequences are listed in Table 4. In particular embodiments, the linker of the fusion molecule of this invention is set forth in SEQ ID NO:36.

TABLE 4

| Linker Sequence | SEQ ID NO: |
|---|---|
| GSSGSSGSSGS | 23 |
| GSNGGFDSSEGG | 24 |
| SSGSSGSSGS | 25 |
| GSSGGSGGSGG | 26 |
| GSSSDSDSSAGS | 27 |
| GSNDSGGSEGG | 28 |
| GSIRWSGLSGGD | 29 |
| GSRGGSVYSEGG | 30 |
| GSSEGSSDFGGD | 31 |
| GSIVVSCSSEGG | 32 |
| GSNWDSGCSREG | 33 |
| GSNWDSGCSREC | 34 |
| GSSGCTGDAGGS | 35 |
| GSNWDSGCSRQC | 36 |
| GSIAGCGDAGEG | 37 |
| GSNWDSGCSRE | 38 |
| GSNWDSGCSREG | 39 |
| NWDSGCSREG | 40 |
| IAGCGDAGEG | 41 |
| SRRASGSSGGSSGTSGSSGGSSGTSTDP | 42 |
| ASGSSGGSSGTSGSSGGSSGTSTDP | 43 |
| GGGGS | 44 |

TABLE 4-continued

| Linker Sequence | SEQ ID NO: |
|---|---|
| GGGGSGGGGS | 45 |
| GGGGSGGGSGGGGS | 46 |
| GSSGSSGSSGSGSSGSSGSSGS | 47 |
| ASGSSGGSSGTS | 48 |

While it has been demonstrated that a type I interferon and type III interferon fusion molecule exhibits anti-tumor activity and is of use in activating antiviral responses, it is contemplated that a type I interferon and/or type III interferon can also be fused to a type II interferon to modulate immune and inflammatory responses as well as inhibit or treat fungal infections and bacterial infections. Type II interferon, also known as IFN-γ, is an anti-parallel homodimer, which binds to the IFN-γ receptor (IFNGR) complex. IFN-γ has some anti-viral and anti-tumor effects, and potentiates the effects of type I and type III IFNs. IFN-γ recruits leukocytes to a site of infection, resulting in increased inflammation. It also stimulates macrophages to kill bacteria that have been engulfed. IFN-γ also regulates the Th2 response. In one embodiment, the type II IFN is a mammalian type II IFN. In another embodiment, the type II IFN is a human type II IFN. Human type II IFN is known in the art under GENBANK Accession No. NP_000610 and has a mature amino acid sequence of:

(SEQ ID NO: 49)
DPYVKEAENLKKYFNAGHSDVADNGTLFLGILKNWKEESDRKIMQSQI

VSFYFKLFKNFKDDQSIQKSVETIKEDMNVKFFNSNKKKRDDFEKLTN

YSVTDLNVQRKAIHELIQVMAELSPAAKTGKRKRSQMLFRGRRASQ

As with the type I and type III IFNs, IFN-γ has a signal peptide, the sequence of which is: MKYTSYILAFQL-CIVLGSLGCYCQ (SEQ ID NO:50). A fusion molecule including type II IFN can have the structure (N→C terminal orientation) of Type II IFN-Linker-Type I IFN; Type I IFN-Linker-Type II IFN; Type II IFN-Linker-Type III IFN; Type III IFN-Linker-Type II IFN; Type I IFN-Linker-Type II IFN-Linker-Type III IFN; Type II IFN-Linker-Type I IFN-Linker-Type III IFN; Type III IFN-Linker-Type II IFN-Linker-Type I IFN; or Type I IFN-Linker-Type III IFN-Linker-Type II IFN.

The fusion molecule of the invention can be produced by conventional recombinant expression methodologies using known expression systems including, but not limited to, *E. coli*, yeast, baculovirus, insect, plant or mammalian protein expression systems. The fusion molecule may be recovered and purified from recombinant cell cultures in any effective manner. For example, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. See, e.g., Lin, et al. (1986) *Meth. Enzymol.* 119: 183-192. Most preferably, high performance liquid chromatography ("HPLC") is employed for purification. Further methods that may be used for production and isolation of the fusion molecule of the present invention are disclosed in U.S. Pat. No. 6,433,145.

In addition, polypeptides of the invention can be chemically synthesized using any effective technique (see, e.g., Creighton (1983) *Proteins: Structures and Molecular Principles*, W. H. Freeman & Co., NY; Hunkapiller, et al. (1984)

*Nature* 310:105-111). For example, the fusion molecule or fragments of fusion molecule can be synthesized with a peptide synthesizer.

The invention also encompasses a fusion molecule, which has been modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The fusion molecule may also be modified with a detectable label, such as an enzymatic, fluorescent, isotopic or affinity label to allow for detection and isolation of the protein.

Also provided by the invention are chemically modified derivatives of the fusion molecule of the invention, which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo, et al. (1996) *Appl. Biochem. Biotechnol.* 56:59-72; Vorobjev, et al. (1999) *Nucleosides Nucleotides* 18:2745-2750; and Caliceti, et al. (1999) *Bioconjug. Chem.* 10:638-646.

Polyethylene glycol molecules (or other chemical moieties) should be attached to the fusion molecule with consideration of effects on functional or antigenic domains of the protein. There are a number of attachment methods available to those skilled in the art, see, e.g., EP 0 401 384, which teaches coupling of PEG to G-CSF, and Malik, et al. (1992) *Exp. Hematol.* 20:1028-1035, which describes pegylation of GM-CSF using tresyl chloride. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the fusion molecule of the invention may be accomplished by any number of means. For example, polyethylene glycol may be attached to the protein either directly or by an intervening linker. Linkerless systems for attaching polyethylene glycol to proteins are described in Delgado et al. (1992) *Crit. Rev. Thera. Drug Carrier Sys.* 9:249-304; Francis, et al. (1998) *Intern. J. Hematol.* 68:1-18; U.S. Pat. Nos. 4,002,531; 5,349,052; WO 95/06058; and WO 98/32466.

The number of polyethylene glycol moieties attached the fusion molecule of the invention (i.e., the degree of substitution) may also vary. For example, the pegylated protein of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado, et al. (1992) *Crit. Rev. Thera. Drug Carrier Sys.* 9:249-304.

As indicated, the fusion molecule of this invention can be used for the treatment of various cancers, viral diseases and other indications. In one nonlimiting embodiment, the fusion molecules is used in n indications where IFN-α or IFN-λ are used such as, but not limited to, fungal infections, bacterial infections, autoimmune conditions and inflammation. Accordingly, the present invention also provides a method for preventing or treating a disease or condition by administering to a subject in need of treatment an effective amount of a type I and type III IFN fusion molecule. In particular embodiments, the disease or condition is one that is a condition which is responsive to IFN-α or IFN-λ.

By "responsive, as used herein it is meant to encompass any cellular response or response by the subject to administration of the interferon which is indicative of the interferon being useful in preventing, ameliorating, reducing, or eliminating one or more signs or symptoms associated with the condition.

For the purposes of the present invention, a "subject" is intended to include a mammal, e.g., a human, non-human primate (e.g., baboon, orangutan, monkey), mouse, pig, cow, goat, cat, rabbit, rat, guinea pig, hamster, horse, monkey, sheep, or other non-human mammal; or a non-mammal, including, e.g., a non-mammalian vertebrate, such as a bird (e.g., a chicken or duck) or a fish, and a non-mammalian invertebrate.

In accordance with the method of the invention, an "effective amount" means a dosage or amount of the fusion molecule or pharmaceutical composition comprising the fusion molecule sufficient to produce a desired result. The desired result may include an objective or subjective improvement in the subject receiving the dosage or amount. In particular, an effective amount is an amount that prevents, ameliorates, reduces, or eliminates one or more signs or symptoms associated with the disease or condition. Treatment can include therapy of an existing condition or prophylaxis of anticipated infections, including but not limited to common recurring infections such as influenza, and circumstances requiring emergency prophylaxis, such as a bioweapon attack.

In some nonlimiting embodiments, the method of the invention is of use in the treatment of a viral infection, such as, but not limited to, Chronic Hepatitis C infection, Chronic Hepatitis B infection and AIDS; cancer, such as but not limited to, Hairy Cell Leukemia, Malignant Melanoma, Hepatocellular Carcinoma, Follicular Lymphoma, AIDS-related Kaposi's Sarcoma, Non-Hodgkin's Lymphoma, Chronic Melogenous Leukemia, Basal Cell Carcinoma, Multiple Myeloma, carcinoid tumors, bladder cancer, Cutaneous T Cell Lymphoma and Renal Cell Carcinoma; an autoimmune condition such as, but not limited to, Crohn's Disease, Multiple Sclerosis and Condylomata Acuminata; inflammation; bacterial infections and fungal infections. In particular nonlimiting embodiments, the fusion molecules and method of the invention is of use in the treatment of a viral infection or cancer. In another nonlimiting embodiment, the fusion molecules and method of the invention is for use in targeting and inhibiting infection in two or more cell types in a subject.

Any effective amount of the fusion molecule of the present invention may be administered to a subject in need thereof, e.g., a subject with a disease or condition or at risk of acquiring the disease or condition. As a general proposition, the total pharmaceutically effective amount administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day. If given continuously, the composition is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur may vary depending on the desired effect.

For therapeutic purposes, the fusion molecule of the invention is preferably provided as a pharmaceutical composition containing the fusion molecule in admixture with a pharmaceutically acceptable carrier. The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier such as a non-toxic solid, semisolid or liquid filler, diluent, encapsulating material or formulation auxiliary of any type.

Pharmaceutical compositions containing the fusion molecule of the invention may be administered by any effective route, including, for example, orally, rectally, parenterally, intracistemally, intravaginally, intraperitoneally, topically (as by powders, ointments, drops or transdermal patch), bucally, or as an oral or nasal spray.

The term "parenteral" as used herein refers to any effective parenteral mode of administration, including modes of administration such as intravenous, intramuscular, intraperitoneal, intrasternal, subcutaneous and intraarticular injection and infusion.

The compositions may also suitably be administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, et al. (1983) *Biopolymers* 22:547-556), poly (2-hydroxyethyl methacrylate) (Langer, et al. (1981) *J. Biomed. Mater. Res.* 15:167-277; Langer (1982) *Chem. Tech.* 12:98-105), ethylene vinyl acetate or poly-D-(−)-3-hydroxybutyric acid (EP 133,988).

In a preferred embodiment, compositions of the invention are formulated in a biodegradable, polymeric drug delivery system, for example as described in U.S. Pat. Nos. 4,938,763; 5,278,201; 5,278,202; 5,324,519; 5,340,849; 5,487,897; WO01/35929; WO00/24374; and WO00/06117. In specific preferred embodiments the compositions of the invention are formulated using the ATRIGEL Biodegradable System of Atrix Laboratories, Inc. (Fort Collins, Colo.).

Examples of biodegradable polymers which can be used in the formulation of compositions of the present invention, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of compositions are poly(lactide-co-glycolides).

Polymer properties such as molecular weight, hydrophobicity, and lactide/glycolide ratio may be modified to obtain the desired drug release profile (See, e.g., Ravivarapu, et al. (2000) *J. Pharmaceut. Sci.* 89:732-741).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alcohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one. Other preferred solvents are benzyl alchohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations containing compositions of the present invention and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl)sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C6-C12 alkanols, 2-ethoxyethanol. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

Sustained-release compositions also include liposomally entrapped polypeptides. Liposomes containing a polypeptide of the present invention are prepared by methods known in the art DE 3,218,121; Epstein, et al. (1985) *Proc. Natl. Acad. Sci. USA* 82:3688-3692; Hwang, et al. (1980) *Proc. Natl. Acad. Sci. USA* 77:4030-4034; EP 52,322; EP 36,676; EP 88,046; EP 143,949; EP 142,641; JP 83-118008; U.S. Pat. Nos. 4,485,045; 4,544,545; and EP 102,324. Ordinarily, the liposomes are of the small (about 200-800 Angstroms), unilamellar type in which the lipid content is greater than about 30 mol. percent cholesterol, the selected proportion being adjusted for effective polypeptide therapy.

The fusion molecule of the present invention may be administered in combination with other known anti-viral, immunomodulatory and anti-proliferative therapies, such as IL-2, KDI, Ribavirin and temozolomide.

The invention also provides a pharmaceutical pack or kit including one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the fusion molecule of the present invention may be employed in conjunction with other therapeutic compounds.

The following nonlimiting examples further illustrate the present invention.

EXAMPLES

Example 1

Figure 23:
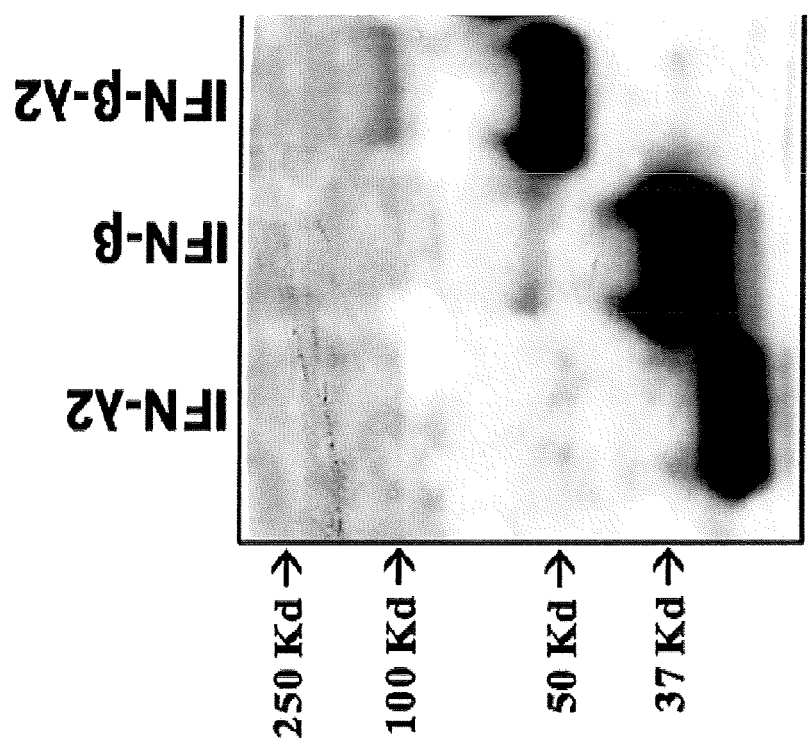
FIG. 23 shows results of the immunoblot with the use of anti-His antibodies for supernatants of HEK293 cells expressing single or fusion mIFN molecules which contain C-terminal 6× His tag for detection and purification.
Figure 24:
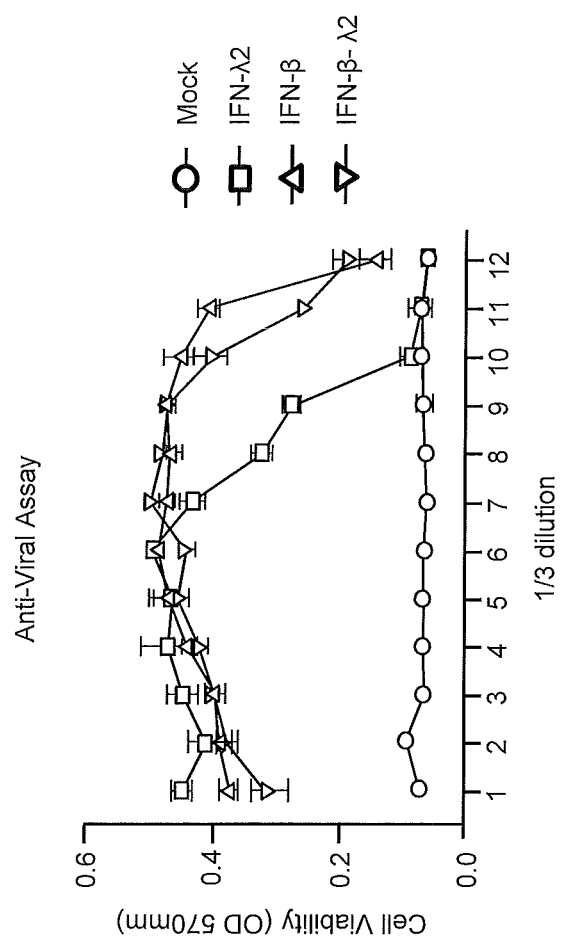
FIG. 24 shows antiviral activities of His-tagged single or fusion mIFN molecules produced in HEK293 cells tested on murine intestinal epithelial cells (mIECs).
Figure 25:
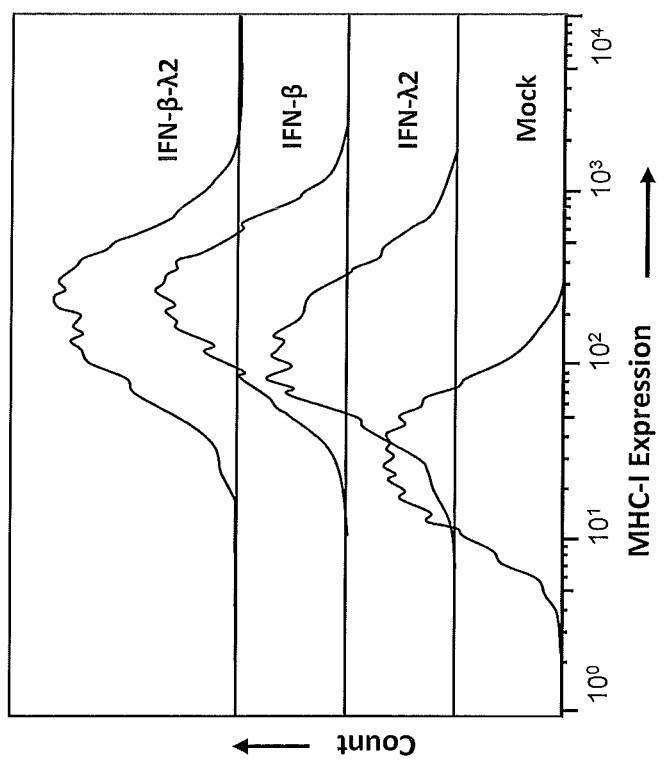
FIG. 25 shows up-regulation of MHC class I antigens in mIECs in response to His-tagged single or fusion mIFN molecules produced in HEK293 cells.

Several IFN fusion molecules have been generated and tested in various assays. These molecules include: i) hIFN-α-hIFN-λ1 (FIG. 12; SEQ ID NO:51); ii) hIFN-α-hIFN-λ3 (FIG. 13; SEQ ID NO:52); iii) hIFN-β-hIFN-λ3 (FIG. 14; SEQ ID NO:53); iv) mIFN-α-mIFN-λ2 (FIG. 21; SEQ ID NO:54); and v) mIFN-β-mIFN-λ2 (FIG. 22; SEQ ID NO:55). Mammalian expression plasmids encoding these fusion molecules were generated with the use of standard PCR and DNA cloning techniques. Some of the constructs, specifically constructs encoding fusion mIFN-β-mIFN-λ2 as well as single mIFN-β and mIFN-λ2 were generated without and with 6× His tag for protein detection and purification. The expression plasmids were transiently transfected into HEK293 cells and their expression levels were evaluated by either immunoblotting with His antibodies (FIG. 23) and/or biological assays (FIGS. 16, 24 and 25).

Example 2

IFN fusion molecules were tested for their ability to induce IFN-specific biological activities, including: i) up-regulation of MHC class I antigen expression (FIG. 25); ii) induction of antiviral protection (FIG. 24); and STAT1 activation (FIG. 16). Human IFN fusion molecules were tested on human retinal pigment epithelial cells or CHO reporter cell lines that express chimeric human type I or type II IFN receptor complexes (FIG. 15). These two separate reporter cell lines exclusively and specifically respond to either human type I or human type III IFNs, whereas parental CHO cells are unresponsive to either type of human IFN. Therefore, these cell lines were used to demonstrate that the IFN fusion molecules retained biological activities of both type I and type III IFNs (FIG. 16). In these experiment, the reporter cells were treated with recombinant human IFN-α or human IFN-λ1, or with condition media from HEK293 cells transiently transfected with plasmid expressing human IFN-α-IFN-λ1 fusion molecule; conditioned media from HEK293 cells transfected with an empty plasmid (mock-transfected) served as a negative control. The reporter cells were treated with IFNs for 15 min, collected and lysed; and STAT1 activation was assessed by electrophoretic mobility shift assay (EMSA). In this assay, STAT1 dimers, which only form upon STAT1 Tyr701 phosphorylation, bind to a specific DNA probe, which is radioactively labeled. The presence of the DNA:protein complex is indicative of STAT1 phosphorylation and activation. STAT1 activation can be also detected by immunoblotting with specific Tyr701 STAT1 antibodies. For this assay, reporter or unmodified human or murine cell lines or primary cells are treated with IFN samples for 15 min, lysed, and immunoblotting is performed. Since mouse type III IFNs can signal through the human type III IFN receptor, CHO reporter cells were used to demonstrate induction of type III IFN signaling by mouse IFN fusion molecules. Mouse fibroblasts respond only to type I IFNs and were used to demonstrate induction of type I IFN signaling by mouse IFN fusion molecules. Human type I and type III IFN responsive human retinal pigment epithelial ARPE-19 cells, and mouse type I and type III IFN responsive murine lung epithelial MLE cells and murine intestinal epithelial cells (mIECs) were also used in these assays. All IFN fusion molecules were tested for their ability to stimulate STAT1 activation in either EMSA and/or immunoblotting on appropriate cell lines and shown to retain activities of both type I and type III IFNs. Fusion IFN molecules will be purified to homogeneity, protein concentrations will be determined and their potencies in STAT1 activation assays will be compared to those of single recombinant IFN molecules.

Example 3

For antiviral assays, either ARPE19 or mIECs and cells were used. The species appropriate cells were pretreated for 24 with serial (1:3) dilutions of HEK293 condition media containing IFN fusion molecule or each IFN alone, or recombinant IFNs. The cells were then challenged with vesicular stomatitis virus (VSV) and cell viability was measured by crystal violet staining (FIG. 24). Upon purification of IFN fusion molecules, additional antiviral assays will be performed to compare antiviral potencies of IFN fusion molecules with those of single recombinant IFN molecules.

Example 4

IFN fusion molecules were also tested for their ability to up-regulate cell surface MHC class I antigen expression. For these assays, appropriate cells were treated with recombinant IFNs, or HEK293 condition media containing IFN fusion molecule or each IFN alone. After 72 hours, cells were collected and levels of MHC class I antigen expression were determined by flow cytometry. IFN-untreated cells or cells treated with conditioned media from mock-transfected HEK293 cells were used as controls. Upon purification of IFN fusion molecules, additional assays will be performed to compare potencies of IFN fusion molecules for the up-regulation of MHC class I antigen expression with those of single recombinant IFN molecules.

Example 5

For animal tumor growth experiments, mouse breast cancer E0771 cells constitutively expressing either single mIFN-β or mIFN-λ2, or fusion mIFN-λ-mIFN-λ2 molecules were generated. The cells were stably transfected with the corresponding expression vectors and G418-resistant cell populations expressing comparable levels of IFN molecules were selected. No changes were observed in growth kinetics of the modified cells in vitro. Next, eight-week-old syngeneic wild-type C57BL/6 (E0771) female virgin mice were injected with $10^5$ parental or modified E0771 breast cancer cells (re-suspended in 50% Matrigel) centrally in the right #4 inguinal mammary fat pad. One cohort of mice was injected with 50:50 mixture of tumors cells expressing either mIFN-β or mIFN-λ2 to compare efficacy of IFN combination to efficacy of IFN fusion molecule. The volume of primary tumors was evaluated every other day and recorded. At day 29 (FIG. 20A) or at day 26 (FIGS. 20B and 20C) animals were sacrificed for final tumor evaluation and histological and immunological analyses.

Example 6

Additional studies in another mammary tumor mouse model, namely 4T1 breast cancer that form mammary tumors when implanted into mammary fat pad of BALB/c mice, mouse strain syngeneic for 4T1 cancer cells, and a mouse model of melanoma in which B16 melanoma cells are implanted SQ into C57BL/6 syngeneic mice will be conducted. The experiments will follow the same protocol described above for the E0771 breast cancer model. The cancer cells will be engineered to constitutively express single mIFN-β or mIFN-λ2, or fusion mIFN-β-mIFN-λ2 molecules. Eight-week-old syngeneic mice will be implanted with parental and modified tumors and the volume of primary tumors will evaluated every other day and recorded. A set of mice will be implanted with 50:50 mixture of tumors cells expressing either mIFN-β or mIFN-λ2 to compare efficacy of IFN combination to efficacy of IFN fusion molecule. When primary tumors in any set of mice reach 1 cm$^3$ volume, all animal cohorts will be sacrificed for final tumor evaluation and histological and immunological analyses. Lung metastasis, if any, will be quantified. Primary tumors, as well as lungs, bones, brain and other major organs will be weighed and half snap-frozen and half fixed for further biochemical and histological analyses to study proliferation (Ki67), apoptosis (Tunnel), micro-vessels (CD31) and PASR staining. Primary tumors will also be assessed by a combination of Nanostring, FACS, and IHC-based methods to probe the cellular frequency of PMNs, DCs, MPhs, NK and T cells in the tumors and at the tumor margins. As such, when primary tumors are removed, part of them will also be used to examine the margins by IF and then enzymatically digested to isolate tumor and tumor-infiltrating cells to profile F4/F80+ MPhs, GR1+ neutrophils, CD11+ DCs, and T cells, myofibroblasts and endothelial cells (PECAM+ cells). Leukocyte (DCs, MPhs, NKs and T cells) infiltration and DC maturation status at the tumor site will be quantified by staining immune cells with specific markers such as CD86 (Alexa 350 labeling) for DCs, F4/F80

(Alexa 405 labeling) for MPhs, and CD4+ (PE-Cy7 labeling) and CD8+ (Alexa 649 labeling) for T cells followed by FACS analysis. Moreover, tumor-associated cytokines and chemokines will be quantified by RT-PCR and measuring protein expression analyzed by custom MSD-cytokine arrays or ELISA. Blood will be collected to test for different tumor-associated cytokines, chemokines, and adipokines associated with inflammatory response and stromal stimulation. If a subset of animals does not develop primary tumors, these tumor-free mice will be injected with parental tumors to test for the development of anti-tumor immunity in these mice. Development of anti-tumor responses will also be evaluated by testing tumoricidal activity of splenocytes in tumor-bearing mice. After tumor formation or the lack of it, cohorts of mice will be sacrificed and splenocytes will be isolated and used to evaluate tumor-induced activation and proliferation of CTLs by measuring IFN-γ production by spleen cells co-cultured in vitro with tumor cells. In addition, ability of splenocytes to kill tumor cells will be assessed by performing a cytotoxicity assay in which splenocytes are co-cultured with $^{51}$Cr-labeled tumor cells and $^{51}$Cr release is measured. Irrelevant tumor cells (B16 for E0771 and vice versa) will be used as controls.

Example 7

Recombinant IFN fusion molecules which are >95% pure endotoxin-free will be tested as cancer therapeutics. Mouse models of breast cancer and melanoma growth described supra will be utilized. Mice will be injected with parental cancer cells and allowed to form tumors ~0.5 cm$^3$. Tumor bearing mice will be IV injected with various doses of IFN fusion molecules, single IFNs or the combination of single IFNs. Effects of IFN therapies on tumor progression and metastasis formation will be monitored as described supra. Various histological and immunological assays described above will be also performed.

Example 8

Antiviral potency of IFN fusion molecules will be tested using a mouse model of influenza A infection and compared to potencies of single IFNs or their 50:50 combination. As a prophylaxis, mice will be injected SQ or intranasally (IN) with various doses (0.1, 0.3, 1, 3, 10 µg per adult ~20 mg eight-week old mouse; PBS will be used as a control mock treatment) 8 or 24 hours preceding infection of mice with 1 LD$_{50}$ of influenza A virus strain PR8, WSN, Udorn or other strains. Survival and weight loss will be monitored daily. In addition, in a separate experiment, viral titers and lung histopathology will be determined at days 3, 6, and 9 post infection. By examination of the histopathology, pathology will be assessed. By IHC staining for viral antigen, determination will be made as to whether treatment has altered the pattern of virus spread. The optimal IFN treatment will be determined for enhancing survival post infection. In this experiment, the effects of treatment after infection with influenza A virus (1 LD$_{50}$ strain PR8, WSN, Udorn or other strains) will be assessed with multiple dosing regimens. As described supra, mice will be treated with IFN fusion molecules, single IFN or their combination injected SQ or intranasally (IN) with various doses (0.1, 0.3, 1, 3, 10 µg per adult ~20 mg eight-week old mouse; PBS will be used as a control mock treatment). Infected mice will be treated according to the following schedules: days 1, 3, 5; 1-4; 2, 4, 6; 2-5. Mice will be analyzed as described supra, to gauge antiviral protection as well as disease.

Example 9

The Mx2-luciferase reporter mouse strain will be used to evaluate induction of ISGs in vivo. Mx2-luciferase transgenic reporter mice have a luciferase reporter gene controlled by IFN-inducible Mx2 promoter. This system allows sensitive in vivo monitoring with the use of whole-body live imaging with the use of Caliper IVIS 200 live animal imaging system. Adult eight-week-old Mx2-luciferase reporter mice will be treated with IFN fusion molecules, single IFN or their combination injected SQ or IN with various doses (0.1, 0.3, 1, 3, 10 µg per adult ~20 mg eight-week old mouse; PBS will be used as a control mock treatment) and luciferase expression will be monitored at 30 min, every hour for 8 hours and at 16, 24, and 48 hours post IFN treatment to determine by live imaging the duration and intensity of IFN stimulation.

Example 10

IHC of various tissues obtained from IFN-treated mice will be performed to measure levels and localization of pSTAT1. STAT1 is a transcriptional factor that is specifically activated (Tyr phosphorylated, pSTAT1) by type I and type III IFNs (FIG. 1) and localizes to the cell nucleus after activation. For these experiments, wild type mice will be treated with IFN fusion molecules, single IFN or their combination injected SQ or IN with various doses (0.1, 0.3, 1, 3, 10 µg per adult ~20 mg eight-week old mouse; PBS will be used as a control mock treatment). Cohorts of animals will be sacrificed at 5 min, 10 min, 15 min, 30 min, every hour for 8 hours and at 16, 24, and 48 hours post IFN treatment. Various tissue including lungs, large and small intestines, kidney, spleen and liver will be dissected, formalin-fixed and paraffin-embedded. After antigen retrieval and blockade of endogenous peroxidase activity performed on deparaffinized 5 micron sections, the sections will be then stained with pSTAT1 antibody (Tyr701). After immunostaining, tissue sections will be counterstained with Mayer's haematoxylin and Scott's bluing buffer. Nuclear localization of pSTAT1 will be examined in various tissues and cell types to assess tissue distribution, cellular targets, intensity and duration of IFN signaling triggered in response to specific IFN treatment regiments with single IFNs, their combination, or IFN fusion molecules.

What is claimed is:

1. A fusion molecule comprising a human type I interferon protein selected from interferon alpha or interferon beta or a fragment shorter in length than the full length interferon protein and which maintains at least a portion of functional activity of the full length protein and/or binding to at least one of the receptor subunits, a human type III interferon protein selected from interferon lambda 1, interferon lambda 2 or interferon lambda 3 or a fragment shorter in length than the full length interferon protein and which maintains at least a portion of the functional activity of the full length protein and/or binding to at least one of the receptor subunits and a linker selected from SEQ ID NO:23, 24, 25, 26, 27, 28, 29, 30, 31, 32, 33, 34, 35, 36, 37, 38, 39, 40, 41, 42, 43, 44, 45, 46, 47, or 48 between the human type I interferon protein or fragment thereof and human type III interferon protein or fragment thereof.

2. The fusion molecule of claim 1, wherein the human type I interferon protein or fragment thereof is human interferon alpha or a fragment thereof.

3. The fusion molecule of claim 2, wherein the human interferon alpha or fragment thereof is human interferon alpha 2 or a fragment thereof.

4. The fusion molecule of claim 1, wherein the human type I interferon protein or fragment thereof is human interferon beta or a fragment thereof.

5. The fusion molecule of claim 1, wherein the human type III interferon protein or fragment thereof is human interferon lambda 1 or a fragment thereof.

6. The fusion molecule of claim 1, wherein the human type III interferon protein or fragment thereof is human interferon lambda 2 or a fragment thereof.

7. The fusion molecule of claim 1, wherein the human type III interferon protein or fragment thereof is human interferon lambda 3 or a fragment thereof.

8. The fusion molecule of claim 1 further comprising a signal peptide at its N-terminus.

9. The fusion molecule of claim 1 comprising a mature portion of the human type I interferon protein or the human type III interferon protein.

10. The fusion molecule of claim 1 comprising an entire sequence inclusive of a signal peptide of the human type I interferon protein or the human type III interferon protein.

11. A pharmaceutical composition comprising the fusion molecule of claim 1 and a pharmaceutically acceptable carrier.

12. A method for treating a disease or condition in a subject, said method comprising administering to the subject an effective amount of the fusion molecule of claim 1 thereby treating the subject's disease or condition, wherein the disease or condition is a viral infection, a fungal infection, a bacterial infection, cancer, an inflammatory disease, or an autoimmune disease.

* * * * *

SEQUENCE LISTING

<160> NUMBER OF SEQ ID NOS: 55

<210> SEQ ID NO 1
<211> LENGTH: 15
<212> TYPE: PRT
<213> ORGANISM: Artificial sequence

```
<220> FEATURE:
<223> OTHER INFORMATION: Synthetic

<400> SEQUENCE: 1

Met Ala Leu Thr Phe Ala Leu Leu Val Ala Leu Leu Val Leu Ser
1               5                   10                  15

<210> SEQ ID NO 2
<211> LENGTH: 22
<212> TYPE: PRT
<213> ORGANISM: Artificial sequence
<220> FEATURE:
<223> OTHER INFORMATION: Synthetic

<400> SEQUENCE: 2

Met Ala Ala Ala Trp Thr Val Val Leu Val Thr Leu Val Leu Gly Leu
1               5                   10                  15

Ala Val Ala Gly Pro Val
            20

<210> SEQ ID NO 3
<211> LENGTH: 22
<212> TYPE: PRT
<213> ORGANISM: Artificial sequence
<220> FEATURE:
<223> OTHER INFORMATION: Synthetic

<400> SEQUENCE: 3

Met Thr Gly Asp Cys Thr Pro Val Leu Val Leu Met Ala Ala Val Leu
1               5                   10                  15

Thr Val Thr Gly Ala Val
            20

<210> SEQ ID NO 4
<211> LENGTH: 22
<212> TYPE: PRT
<213> ORGANISM: Artificial sequence
<220> FEATURE:
<223> OTHER INFORMATION: Synthetic

<400> SEQUENCE: 4

Met Thr Gly Asp Cys Met Pro Val Leu Val Leu Met Ala Ala Val Leu
1               5                   10                  15

Thr Val Thr Gly Ala Val
            20

<210> SEQ ID NO 5
<211> LENGTH: 21
<212> TYPE: PRT
<213> ORGANISM: Artificial sequence
<220> FEATURE:
<223> OTHER INFORMATION: Synthetic

<400> SEQUENCE: 5

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 6
<211> LENGTH: 25
<212> TYPE: PRT
<213> ORGANISM: Artificial sequence
<220> FEATURE:
<223> OTHER INFORMATION: Synthetic
```

```
<400> SEQUENCE: 6

Met Leu Lys Arg Ser Ser Trp Leu Ala Thr Leu Gly Leu Leu Thr Val
1               5                   10                  15

Ala Ser Val Ser Thr Ile Val Tyr Ala
            20                  25

<210> SEQ ID NO 7
<211> LENGTH: 23
<212> TYPE: PRT
<213> ORGANISM: Artificial sequence
<220> FEATURE:
<223> OTHER INFORMATION: Synthetic

<400> SEQUENCE: 7

Met Lys Lys Ala Thr Phe Ile Thr Cys Leu Leu Ala Val Leu Leu Val
1               5                   10                  15

Ser Asn Pro Ile Trp Asn Ala
            20

<210> SEQ ID NO 8
<211> LENGTH: 23
<212> TYPE: PRT
<213> ORGANISM: Artificial sequence
<220> FEATURE:
<223> OTHER INFORMATION: Synthetic

<400> SEQUENCE: 8

Met Lys Val Ser Ala Ala Ala Leu Ala Val Ile Leu Ile Ala Thr Ala
1               5                   10                  15

Leu Cys Ala Pro Ala Ser Ala
            20

<210> SEQ ID NO 9
<211> LENGTH: 23
<212> TYPE: PRT
<213> ORGANISM: Artificial sequence
<220> FEATURE:
<223> OTHER INFORMATION: Synthetic

<400> SEQUENCE: 9

Met Lys Val Ser Thr Ala Phe Leu Cys Leu Leu Leu Thr Val Ser Ala
1               5                   10                  15

Phe Ser Ala Gln Val Leu Ala
            20

<210> SEQ ID NO 10
<211> LENGTH: 18
<212> TYPE: PRT
<213> ORGANISM: Artificial sequence
<220> FEATURE:
<223> OTHER INFORMATION: Synthetic

<400> SEQUENCE: 10

Met Lys Cys Leu Leu Leu Ala Leu Gly Leu Ala Leu Ala Cys Ala Ala
1               5                   10                  15

Gln Ala

<210> SEQ ID NO 11
<211> LENGTH: 23
<212> TYPE: PRT
<213> ORGANISM: Artificial sequence
<220> FEATURE:
<223> OTHER INFORMATION: Synthetic
```

```
<400> SEQUENCE: 11

Met Ala Arg Leu Cys Ala Phe Leu Met Thr Leu Leu Val Met Ser Tyr
1               5                   10                  15

Trp Ser Thr Cys Ser Leu Gly
            20

<210> SEQ ID NO 12
<211> LENGTH: 21
<212> TYPE: PRT
<213> ORGANISM: Artificial sequence
<220> FEATURE:
<223> OTHER INFORMATION: Synthetic

<400> SEQUENCE: 12

Met Asn Asn Arg Trp Ile Leu His Ala Ala Phe Leu Leu Cys Phe Ser
1               5                   10                  15

Thr Thr Ala Leu Ser
            20

<210> SEQ ID NO 13
<211> LENGTH: 173
<212> TYPE: PRT
<213> ORGANISM: Homo sapien

<400> SEQUENCE: 13

Cys Lys Ser Ser Cys Ser Val Gly Cys Asp Leu Pro Gln Thr His Ser
1               5                   10                  15

Leu Gly Ser Arg Arg Thr Leu Met Leu Leu Ala Gln Met Arg Arg Ile
            20                  25                  30

Ser Leu Phe Ser Cys Leu Lys Asp Arg His Asp Phe Gly Phe Pro Gln
        35                  40                  45

Glu Glu Phe Gly Asn Gln Phe Gln Lys Ala Glu Thr Ile Pro Val Leu
    50                  55                  60

His Glu Met Ile Gln Gln Ile Phe Asn Leu Phe Ser Thr Lys Asp Ser
65                  70                  75                  80

Ser Ala Ala Trp Asp Glu Thr Leu Leu Asp Lys Phe Tyr Thr Glu Leu
                85                  90                  95

Tyr Gln Gln Leu Asn Asp Leu Glu Ala Cys Val Ile Gln Gly Val Gly
            100                 105                 110

Val Thr Glu Thr Pro Leu Met Lys Glu Asp Ser Ile Leu Ala Val Arg
        115                 120                 125

Lys Tyr Phe Gln Arg Ile Thr Leu Tyr Leu Lys Glu Lys Lys Tyr Ser
    130                 135                 140

Pro Cys Ala Trp Glu Val Val Arg Ala Glu Ile Met Arg Ser Phe Ser
145                 150                 155                 160

Leu Ser Thr Asn Leu Gln Glu Ser Leu Arg Ser Lys Glu
                165                 170

<210> SEQ ID NO 14
<211> LENGTH: 173
<212> TYPE: PRT
<213> ORGANISM: Homo sapien

<400> SEQUENCE: 14

Cys Lys Ser Ser Cys Ser Val Gly Cys Asp Leu Pro Gln Thr His Ser
1               5                   10                  15

Leu Gly Ser Arg Arg Thr Leu Met Leu Leu Ala Gln Met Arg Arg Ile
            20                  25                  30
```

```
Ser Leu Phe Ser Cys Leu Lys Asp Arg His Asp Phe Gly Phe Pro Gln
            35                  40                  45

Glu Glu Phe Gly Asn Gln Phe Gln Lys Ala Glu Thr Ile Pro Val Leu
 50                  55                  60

His Glu Met Ile Gln Leu Ile Phe Asn Leu Phe Ser Thr Lys Asp Ser
 65                  70                  75                  80

Ser Ala Ala Trp Asp Glu Thr Leu Leu Asp Lys Phe Tyr Thr Glu Leu
                 85                  90                  95

Tyr Gln Gln Leu Asn Asp Leu Glu Ala Cys Val Ile Gln Gly Val Gly
            100                 105                 110

Val Thr Glu Thr Pro Leu Met Lys Glu Asp Ser Ile Leu Ala Val Arg
            115                 120                 125

Lys Tyr Phe Gln Arg Ile Thr Leu Tyr Leu Lys Glu Lys Lys Tyr Ser
            130                 135                 140

Pro Cys Ala Trp Glu Val Val Arg Ala Glu Ile Met Arg Ser Phe Ser
145                 150                 155                 160

Leu Ser Thr Asn Leu Gln Glu Ser Leu Arg Ser Lys Glu
                165                 170

<210> SEQ ID NO 15
<211> LENGTH: 166
<212> TYPE: PRT
<213> ORGANISM: Homo sapien

<400> SEQUENCE: 15

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
 50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 16
<211> LENGTH: 180
<212> TYPE: PRT
<213> ORGANISM: Homo sapien
```

<400> SEQUENCE: 16

```
Pro Val Pro Thr Ser Lys Pro Thr Pro Thr Gly Lys Gly Cys His Ile
1               5                   10                  15

Gly Arg Phe Lys Ser Leu Ser Pro Gln Glu Leu Ala Ser Phe Lys Lys
            20                  25                  30

Ala Arg Asp Ala Leu Glu Glu Ser Leu Lys Leu Lys Asn Trp Ser Cys
        35                  40                  45

Ser Ser Pro Val Phe Pro Gly Asn Trp Asp Leu Arg Leu Leu Gln Val
    50                  55                  60

Arg Glu Arg Pro Val Ala Leu Glu Ala Glu Leu Ala Leu Thr Leu Lys
65                  70                  75                  80

Val Leu Glu Ala Ala Ala Gly Pro Ala Leu Glu Asp Val Leu Asp Gln
                85                  90                  95

Pro Leu His Thr Leu His His Ile Leu Ser Gln Leu Gln Ala Cys Ile
            100                 105                 110

Gln Pro Gln Pro Thr Ala Gly Pro Arg Pro Arg Gly Arg Leu His His
        115                 120                 125

Trp Leu His Arg Leu Gln Glu Ala Pro Lys Lys Glu Ser Ala Gly Cys
    130                 135                 140

Leu Glu Ala Ser Val Thr Phe Asn Leu Phe Arg Leu Leu Thr Arg Asp
145                 150                 155                 160

Leu Lys Tyr Val Ala Asp Gly Asn Leu Cys Leu Arg Thr Ser Thr His
                165                 170                 175

Pro Glu Ser Thr
            180
```

<210> SEQ ID NO 17
<211> LENGTH: 180
<212> TYPE: PRT
<213> ORGANISM: Homo sapien

<400> SEQUENCE: 17

```
Pro Val Pro Thr Ser Lys Pro Thr Thr Thr Gly Lys Gly Cys His Ile
1               5                   10                  15

Gly Arg Phe Lys Ser Leu Ser Pro Gln Glu Leu Ala Ser Phe Lys Lys
            20                  25                  30

Ala Arg Asp Ala Leu Glu Glu Ser Leu Lys Leu Lys Asn Trp Ser Cys
        35                  40                  45

Ser Ser Pro Val Phe Pro Gly Asn Trp Asp Leu Arg Leu Leu Gln Val
    50                  55                  60

Arg Glu Arg Pro Val Ala Leu Glu Ala Glu Leu Ala Leu Thr Leu Lys
65                  70                  75                  80

Val Leu Glu Ala Ala Ala Gly Pro Ala Leu Glu Asp Val Leu Asp Gln
                85                  90                  95

Pro Leu His Thr Leu His His Ile Leu Ser Gln Leu Gln Ala Cys Ile
            100                 105                 110

Gln Pro Gln Pro Thr Ala Gly Pro Arg Pro Arg Gly Arg Leu His His
        115                 120                 125

Trp Leu His Arg Leu Gln Glu Ala Pro Lys Lys Glu Ser Ala Gly Cys
    130                 135                 140

Leu Glu Ala Ser Val Thr Phe Asn Leu Phe Arg Leu Leu Thr Arg Asp
145                 150                 155                 160
```

```
Leu Lys Tyr Val Ala Asp Gly Asn Leu Cys Leu Arg Thr Ser Thr His
                165                 170                 175

Pro Glu Ser Thr
            180

<210> SEQ ID NO 18
<211> LENGTH: 174
<212> TYPE: PRT
<213> ORGANISM: Homo sapien

<400> SEQUENCE: 18

Pro Val Ala Arg Leu His Gly Ala Leu Pro Asp Ala Arg Gly Cys His
1               5                   10                  15

Ile Ala Gln Phe Lys Ser Leu Ser Pro Gln Glu Leu Gln Ala Phe Lys
                20                  25                  30

Arg Ala Lys Asp Ala Leu Glu Glu Ser Leu Leu Leu Lys Asp Cys Arg
            35                  40                  45

Cys His Ser Arg Leu Phe Pro Arg Thr Trp Asp Leu Arg Gln Leu Gln
        50                  55                  60

Val Arg Glu Arg Pro Met Ala Leu Glu Ala Glu Leu Ala Leu Thr Leu
65                  70                  75                  80

Lys Val Leu Glu Ala Thr Ala Asp Thr Asp Pro Ala Leu Val Asp Val
                85                  90                  95

Leu Asp Gln Pro Leu His Thr Leu His His Ile Leu Ser Gln Phe Arg
            100                 105                 110

Ala Cys Ile Gln Pro Gln Pro Thr Ala Gly Pro Arg Thr Arg Gly Arg
        115                 120                 125

Leu His His Trp Leu Tyr Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Val
                165                 170

<210> SEQ ID NO 19
<211> LENGTH: 174
<212> TYPE: PRT
<213> ORGANISM: Homo sapien

<400> SEQUENCE: 19

Pro Val Ala Arg Leu His Gly Ala Leu Pro Asp Ala Arg Gly Cys His
1               5                   10                  15

Ile Ala Gln Phe Lys Ser Leu Ser Pro Gln Glu Leu Gln Ala Phe Lys
                20                  25                  30

Arg Ala Lys Asp Ala Leu Glu Glu Ser Leu Leu Leu Lys Asp Cys Arg
            35                  40                  45

Cys His Ser Arg Leu Phe Pro Arg Thr Trp Asp Leu Arg Gln Leu Gln
        50                  55                  60

Val Arg Glu Arg Pro Met Ala Leu Glu Ala Glu Leu Ala Leu Thr Leu
65                  70                  75                  80

Lys Val Leu Glu Ala Thr Ala Asp Thr Asp Pro Ala Leu Val Asp Val
                85                  90                  95

Leu Asp Gln Pro Leu His Thr Leu His His Ile Leu Ser Gln Phe Arg
            100                 105                 110

Ala Cys Ile Gln Pro Gln Pro Thr Ala Gly Pro Arg Ala Arg Gly Arg
        115                 120                 125
```

```
Leu His His Trp Leu Tyr Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Val
                165                 170

<210> SEQ ID NO 20
<211> LENGTH: 174
<212> TYPE: PRT
<213> ORGANISM: Homo sapien

<400> SEQUENCE: 20

Pro Val Ala Arg Leu Arg Gly Ala Leu Pro Asp Ala Arg Gly Cys His
1               5                   10                  15

Ile Ala Gln Phe Lys Ser Leu Ser Pro Gln Glu Leu Gln Ala Phe Lys
                20                  25                  30

Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
        50                  55                  60

Val Arg Glu Arg Pro Val Ala Leu Glu Ala Glu Leu Ala Leu Thr Leu
65                  70                  75                  80

Lys Val Leu Glu Ala Ser Ala Asp Thr Asp Pro Ala Leu Gly Asp Val
                85                  90                  95

Leu Asp Gln Pro Leu His Thr Leu His His Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His His Trp Leu Tyr Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Val
                165                 170

<210> SEQ ID NO 21
<211> LENGTH: 174
<212> TYPE: PRT
<213> ORGANISM: Homo sapien

<400> SEQUENCE: 21

Pro Val Ala Arg Leu Arg Gly Ala Leu Pro Asp Ala Arg Gly Cys His
1               5                   10                  15

Ile Ala Gln Phe Lys Ser Leu Ser Pro Gln Glu Leu Gln Ala Phe Lys
                20                  25                  30

Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
        50                  55                  60

Val Arg Glu Arg Pro Val Ala Leu Glu Ala Glu Leu Ala Leu Thr Leu
65                  70                  75                  80

Lys Val Leu Glu Ala Thr Ala Asp Thr Asp Pro Ala Leu Gly Asp Val
                85                  90                  95

Leu Asp Gln Pro Leu His Thr Leu His His Ile Leu Ser Gln Leu Arg
                100                 105                 110
```

Ala Cys Ile Gln Pro Gln Pro Thr Ala Gly Pro Arg Thr Arg Gly Arg
            115                 120                 125

Leu His His Trp Leu His Arg Leu Gln Glu Ala Pro Lys Lys Glu Ser
        130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Val
                165                 170

<210> SEQ ID NO 22
<211> LENGTH: 156
<212> TYPE: PRT
<213> ORGANISM: Homo sapien

<400> SEQUENCE: 22

Pro Arg Arg Cys Leu Leu Ser His Tyr Arg Ser Leu Glu Pro Arg Thr
1               5                   10                  15

Leu Ala Ala Ala Lys Ala Leu Arg Asp Arg Tyr Glu Glu Glu Ala Leu
            20                  25                  30

Ser Trp Gly Gln Arg Asn Cys Ser Phe Arg Pro Arg Arg Asp Pro Pro
        35                  40                  45

Arg Pro Ser Ser Cys Ala Arg Leu Arg His Val Ala Arg Gly Ile Ala
    50                  55                  60

Asp Ala Gln Ala Val Leu Ser Gly Leu His Arg Ser Glu Leu Leu Pro
65                  70                  75                  80

Gly Ala Gly Pro Ile Leu Glu Leu Leu Ala Ala Gly Arg Asp Val
                85                  90                  95

Ala Ala Cys Leu Glu Leu Ala Arg Pro Gly Ser Ser Arg Lys Val Pro
            100                 105                 110

Gly Ala Gln Lys Arg Arg His Lys Pro Arg Arg Ala Asp Ser Pro Arg
        115                 120                 125

Cys Arg Lys Ala Ser Val Val Phe Asn Leu Arg Leu Leu Thr Trp
    130                 135                 140

Glu Leu Arg Leu Ala Ala His Ser Gly Pro Cys Leu
145                 150                 155

<210> SEQ ID NO 23
<211> LENGTH: 11
<212> TYPE: PRT
<213> ORGANISM: Artificial sequence
<220> FEATURE:
<223> OTHER INFORMATION: Synthetic

<400> SEQUENCE: 23

Gly Ser Ser Gly Ser Ser Gly Ser Ser Gly Ser
1               5                   10

<210> SEQ ID NO 24
<211> LENGTH: 12
<212> TYPE: PRT
<213> ORGANISM: Artificial sequence
<220> FEATURE:
<223> OTHER INFORMATION: Synthetic

<400> SEQUENCE: 24

Gly Ser Asn Gly Gly Phe Asp Ser Ser Glu Gly Gly
1               5                   10

```
<210> SEQ ID NO 25
<211> LENGTH: 10
<212> TYPE: PRT
<213> ORGANISM: Artificial sequence
<220> FEATURE:
<223> OTHER INFORMATION: Synthetic

<400> SEQUENCE: 25

Ser Ser Gly Ser Ser Gly Ser Ser Gly Ser
1               5                   10

<210> SEQ ID NO 26
<211> LENGTH: 12
<212> TYPE: PRT
<213> ORGANISM: Artificial sequence
<220> FEATURE:
<223> OTHER INFORMATION: Synthetic

<400> SEQUENCE: 26

Gly Ser Ser Gly Gly Ser Gly Gly Ser Gly Gly Gly
1               5                   10

<210> SEQ ID NO 27
<211> LENGTH: 12
<212> TYPE: PRT
<213> ORGANISM: Artificial sequence
<220> FEATURE:
<223> OTHER INFORMATION: Synthetic

<400> SEQUENCE: 27

Gly Ser Ser Ser Asp Ser Asp Ser Ser Ala Gly Ser
1               5                   10

<210> SEQ ID NO 28
<211> LENGTH: 12
<212> TYPE: PRT
<213> ORGANISM: Artificial sequence
<220> FEATURE:
<223> OTHER INFORMATION: Synthetic

<400> SEQUENCE: 28

Gly Ser Asn Asp Ser Ser Gly Gly Ser Glu Gly Gly
1               5                   10

<210> SEQ ID NO 29
<211> LENGTH: 12
<212> TYPE: PRT
<213> ORGANISM: Artificial sequence
<220> FEATURE:
<223> OTHER INFORMATION: Synthetic

<400> SEQUENCE: 29

Gly Ser Ile Arg Trp Ser Gly Leu Ser Gly Gly Asp
1               5                   10

<210> SEQ ID NO 30
<211> LENGTH: 12
<212> TYPE: PRT
<213> ORGANISM: Artificial sequence
<220> FEATURE:
<223> OTHER INFORMATION: Synthetic

<400> SEQUENCE: 30

Gly Ser Arg Gly Gly Ser Val Tyr Ser Glu Gly Gly
1               5                   10
```

```
<210> SEQ ID NO 31
<211> LENGTH: 12
<212> TYPE: PRT
<213> ORGANISM: Artificial sequence
<220> FEATURE:
<223> OTHER INFORMATION: Synthetic

<400> SEQUENCE: 31

Gly Ser Ser Glu Gly Ser Ser Asp Phe Gly Gly Asp
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic

<400> SEQUENCE: 32

Gly Ser Ile Val Val Ser Cys Ser Ser Glu Gly Gly
1               5                   10

<210> SEQ ID NO 33
<211> LENGTH: 12
<212> TYPE: PRT
<213> ORGANISM: Artificial sequence
<220> FEATURE:
<223> OTHER INFORMATION: Synthetic

<400> SEQUENCE: 33

Gly Ser Asn Trp Asp Ser Gly Cys Ser Arg Glu Gly
1               5                   10

<210> SEQ ID NO 34
<211> LENGTH: 12
<212> TYPE: PRT
<213> ORGANISM: Artificial sequence
<220> FEATURE:
<223> OTHER INFORMATION: Synthetic

<400> SEQUENCE: 34

Gly Ser Asn Trp Asp Ser Gly Cys Ser Arg Glu Cys
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic

<400> SEQUENCE: 35

Gly Ser Ser Gly Cys Thr Gly Asp Ala Gly Gly Ser
1               5                   10

<210> SEQ ID NO 36
<211> LENGTH: 12
<212> TYPE: PRT
<213> ORGANISM: Artificial sequence
<220> FEATURE:
<223> OTHER INFORMATION: Synthetic

<400> SEQUENCE: 36

Gly Ser Asn Trp Asp Ser Gly Cys Ser Arg Gln Cys
1               5                   10
```

```
<210> SEQ ID NO 37
<211> LENGTH: 12
<212> TYPE: PRT
<213> ORGANISM: Artificial sequence
<220> FEATURE:
<223> OTHER INFORMATION: Synthetic

<400> SEQUENCE: 37

Gly Ser Ile Ala Gly Cys Gly Asp Ala Gly Glu Gly
1               5                   10

<210> SEQ ID NO 38
<211> LENGTH: 11
<212> TYPE: PRT
<213> ORGANISM: Artificial sequence
<220> FEATURE:
<223> OTHER INFORMATION: Synthetic

<400> SEQUENCE: 38

Gly Ser Asn Trp Asp Ser Gly Cys Ser Arg Glu
1               5                   10

<210> SEQ ID NO 39
<211> LENGTH: 12
<212> TYPE: PRT
<213> ORGANISM: Artificial sequence
<220> FEATURE:
<223> OTHER INFORMATION: Synthetic

<400> SEQUENCE: 39

Gly Ser Asn Trp Asp Ser Gly Cys Ser Arg Glu Gly
1               5                   10

<210> SEQ ID NO 40
<211> LENGTH: 10
<212> TYPE: PRT
<213> ORGANISM: Artificial sequence
<220> FEATURE:
<223> OTHER INFORMATION: Synthetic

<400> SEQUENCE: 40

Asn Trp Asp Ser Gly Cys Ser Arg Glu Gly
1               5                   10

<210> SEQ ID NO 41
<211> LENGTH: 10
<212> TYPE: PRT
<213> ORGANISM: Artificial sequence
<220> FEATURE:
<223> OTHER INFORMATION: Synthetic

<400> SEQUENCE: 41

Ile Ala Gly Cys Gly Asp Ala Gly Glu Gly
1               5                   10

<210> SEQ ID NO 42
<211> LENGTH: 28
<212> TYPE: PRT
<213> ORGANISM: Artificial sequence
<220> FEATURE:
<223> OTHER INFORMATION: Synthetic

<400> SEQUENCE: 42

Ser Arg Arg Ala Ser Gly Ser Ser Gly Gly Ser Ser Gly Thr Ser Gly
1               5                   10                  15

Ser Ser Gly Gly Ser Ser Gly Thr Ser Thr Asp Pro
            20                  25
```

<210> SEQ ID NO 43
<211> LENGTH: 25
<212> TYPE: PRT
<213> ORGANISM: Artificial sequence
<220> FEATURE:
<223> OTHER INFORMATION: Synthetic

<400> SEQUENCE: 43

Ala Ser Gly Ser Ser Gly Gly Ser Ser Gly Thr Ser Gly Ser Ser Gly
1               5                   10                  15

Gly Ser Ser Gly Thr Ser Thr Asp Pro
            20                  25

<210> SEQ ID NO 44
<211> LENGTH: 5
<212> TYPE: PRT
<213> ORGANISM: Artificial sequence
<220> FEATURE:
<223> OTHER INFORMATION: Synthetic

<400> SEQUENCE: 44

Gly Gly Gly Gly Ser
1               5

<210> SEQ ID NO 45
<211> LENGTH: 10
<212> TYPE: PRT
<213> ORGANISM: Artificial sequence
<220> FEATURE:
<223> OTHER INFORMATION: Synthetic

<400> SEQUENCE: 45

Gly Gly Gly Gly Ser Gly Gly Gly Gly Ser
1               5                   10

<210> SEQ ID NO 46
<211> LENGTH: 14
<212> TYPE: PRT
<213> ORGANISM: Artificial sequence
<220> FEATURE:
<223> OTHER INFORMATION: Synthetic

<400> SEQUENCE: 46

Gly Gly Gly Gly Ser Gly Gly Gly Ser Gly Gly Gly Gly Ser
1               5                   10

<210> SEQ ID NO 47
<211> LENGTH: 22
<212> TYPE: PRT
<213> ORGANISM: Artificial sequence
<220> FEATURE:
<223> OTHER INFORMATION: Synthetic

<400> SEQUENCE: 47

Gly Ser Ser Gly Ser Ser Gly Ser Ser Gly Ser Gly Ser Ser Gly Ser
1               5                   10                  15

Ser Gly Ser Ser Gly Ser
            20

<210> SEQ ID NO 48
<211> LENGTH: 12
<212> TYPE: PRT
<213> ORGANISM: Artificial sequence
<220> FEATURE:
<223> OTHER INFORMATION: Synthetic

```
<400> SEQUENCE: 48

Ala Ser Gly Ser Ser Gly Gly Ser Ser Gly Thr Ser
1               5                   10

<210> SEQ ID NO 49
<211> LENGTH: 142
<212> TYPE: PRT
<213> ORGANISM: Homo sapien

<400> SEQUENCE: 49

Asp Pro Tyr Val Lys Glu Ala Glu Asn Leu Lys Lys Tyr Phe Asn Ala
1               5                   10                  15

Gly His Ser Asp Val Ala Asp Asn Gly Thr Leu Phe Leu Gly Ile Leu
            20                  25                  30

Lys Asn Trp Lys Glu Glu Ser Asp Arg Lys Ile Met Gln Ser Gln Ile
        35                  40                  45

Val Ser Phe Tyr Phe Lys Leu Phe Lys Asn Phe Lys Asp Asp Gln Ser
    50                  55                  60

Ile Gln Lys Ser Val Glu Thr Ile Lys Glu Asp Met Asn Val Lys Phe
65                  70                  75                  80

Phe Asn Ser Asn Lys Lys Arg Asp Asp Phe Glu Lys Leu Thr Asn
                85                  90                  95

Tyr Ser Val Thr Asp Leu Asn Val Gln Arg Lys Ala Ile His Glu Leu
            100                 105                 110

Ile Gln Val Met Ala Glu Leu Ser Pro Ala Ala Lys Thr Gly Lys Arg
        115                 120                 125

Lys Arg Ser Gln Met Leu Phe Arg Gly Arg Arg Ala Ser Gln
    130                 135                 140

<210> SEQ ID NO 50
<211> LENGTH: 24
<212> TYPE: PRT
<213> ORGANISM: Artificial sequence
<220> FEATURE:
<223> OTHER INFORMATION: Synthetic

<400> SEQUENCE: 50

Met Lys Tyr Thr Ser Tyr Ile Leu Ala Phe Gln Leu Cys Ile Val Leu
1               5                   10                  15

Gly Ser Leu Gly Cys Tyr Cys Gln
            20

<210> SEQ ID NO 51
<211> LENGTH: 395
<212> TYPE: PRT
<213> ORGANISM: Artificial sequence
<220> FEATURE:
<223> OTHER INFORMATION: Synthetic

<400> SEQUENCE: 51

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60
```

```
Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu Ser Arg Arg Ala
            180                 185                 190

Ser Gly Ser Ser Gly Ser Ser Gly Thr Ser Gly Ser Ser Gly Gly
        195                 200                 205

Ser Ser Gly Thr Ser Thr Asp Pro Val Pro Thr Ser Lys Pro Thr Pro
    210                 215                 220

Thr Gly Lys Gly Cys His Ile Gly Arg Phe Lys Ser Leu Ser Pro Gln
225                 230                 235                 240

Glu Leu Ala Ser Phe Lys Lys Ala Arg Asp Ala Leu Glu Glu Ser Leu
                245                 250                 255

Lys Leu Lys Asn Trp Ser Cys Ser Ser Pro Val Phe Pro Gly Asn Trp
            260                 265                 270

Asp Leu Arg Leu Leu Gln Val Arg Glu Arg Pro Val Ala Leu Glu Ala
        275                 280                 285

Glu Leu Ala Leu Thr Leu Lys Val Leu Glu Ala Ala Gly Pro Ala
    290                 295                 300

Leu Glu Asp Val Leu Asp Gln Pro Leu His Thr Leu His His Ile Leu
305                 310                 315                 320

Ser Gln Leu Gln Ala Cys Ile Gln Pro Gln Pro Thr Ala Gly Pro Arg
                325                 330                 335

Pro Arg Gly Arg Leu His His Trp Leu His Arg Leu Gln Glu Ala Pro
            340                 345                 350

Lys Lys Glu Ser Ala Gly Cys Leu Glu Ala Ser Val Thr Phe Asn Leu
        355                 360                 365

Phe Arg Leu Leu Thr Arg Asp Leu Lys Tyr Val Ala Asp Gly Asn Leu
    370                 375                 380

Cys Leu Arg Thr Ser Thr His Pro Glu Ser Thr
385                 390                 395

<210> SEQ ID NO 52
<211> LENGTH: 389
<212> TYPE: PRT
<213> ORGANISM: Artificial sequence
<220> FEATURE:
<223> OTHER INFORMATION: Synthetic

<400> SEQUENCE: 52

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
                20                  25                  30
```

```
Gly Ser Arg Arg Thr Leu Met Leu Leu Ala Gln Met Arg Ile Ser
            35                  40                  45

Leu Phe Ser Cys Leu Lys Asp Arg His Asp Phe Gly Phe Pro Gln Glu
 50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu Ser Arg Arg Ala
            180                 185                 190

Ser Gly Ser Ser Gly Gly Ser Ser Gly Thr Ser Gly Ser Ser Gly Gly
        195                 200                 205

Ser Ser Gly Thr Ser Thr Asp Pro Val Ala Arg Leu Arg Gly Ala Leu
    210                 215                 220

Pro Asp Ala Arg Gly Cys His Ile Ala Gln Phe Lys Ser Leu Ser Pro
225                 230                 235                 240

Gln Glu Leu Gln Ala Phe Lys Arg Ala Lys Asp Ala Leu Glu Glu Ser
                245                 250                 255

Leu Leu Leu Lys Asp Cys Lys Cys Arg Ser Arg Leu Phe Pro Arg Thr
            260                 265                 270

Trp Asp Leu Arg Gln Leu Gln Val Arg Glu Arg Pro Val Ala Leu Glu
        275                 280                 285

Ala Glu Leu Ala Leu Thr Leu Lys Val Leu Glu Ala Ser Ala Asp Thr
290                 295                 300

Asp Pro Ala Leu Gly Asp Val Leu Asp Gln Pro Leu His Thr Leu His
305                 310                 315                 320

His Ile Leu Ser Gln Leu Arg Ala Cys Ile Gln Pro Gln Pro Thr Ala
                325                 330                 335

Gly Pro Arg Thr Arg Gly Arg Leu His His Trp Leu Tyr Arg Leu Gln
            340                 345                 350

Glu Ala Pro Lys Lys Glu Ser Pro Gly Cys Leu Glu Ala Ser Val Thr
        355                 360                 365

Phe Asn Leu Phe Arg Leu Leu Thr Arg Asp Leu Asn Cys Val Ala Ser
    370                 375                 380

Gly Asp Leu Cys Val
385

<210> SEQ ID NO 53
<211> LENGTH: 385
<212> TYPE: PRT
<213> ORGANISM: Artificial sequence
<220> FEATURE:
<223> OTHER INFORMATION: Synthetic
```

<400> SEQUENCE: 53

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
            35                  40                  45

Leu Glu Tyr Cys Leu Lys Asp Arg Met Asn Phe Asp Ile Pro Glu Glu
        50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Ala Ser Gly Ser Ser
            180                 185                 190

Gly Gly Ser Ser Gly Thr Ser Gly Ser Ser Gly Ser Ser Gly Thr
        195                 200                 205

Ser Thr Asp Pro Val Ala Arg Leu Arg Gly Ala Leu Pro Asp Ala Arg
    210                 215                 220

Gly Cys His Ile Ala Gln Phe Lys Ser Leu Ser Pro Gln Glu Leu Gln
225                 230                 235                 240

Ala Phe Lys Arg Ala Lys Asp Ala Leu Glu Glu Ser Leu Leu Leu Lys
                245                 250                 255

Asp Cys Lys Cys Arg Ser Arg Leu Phe Pro Arg Thr Trp Asp Leu Arg
            260                 265                 270

Gln Leu Gln Val Arg Glu Arg Pro Val Ala Leu Glu Ala Glu Leu Ala
        275                 280                 285

Leu Thr Leu Lys Val Leu Glu Ala Ser Ala Asp Thr Asp Pro Ala Leu
290                 295                 300

Gly Asp Val Leu Asp Gln Pro Leu His Thr Leu His His Ile Leu Ser
305                 310                 315                 320

Gln Leu Arg Ala Cys Ile Gln Pro Gln Pro Thr Ala Gly Pro Arg Thr
                325                 330                 335

Arg Gly Arg Leu His His Trp Leu Tyr Arg Leu Gln Glu Ala Pro Lys
            340                 345                 350

Lys Glu Ser Pro Gly Cys Leu Glu Ala Ser Val Thr Phe Asn Leu Phe
        355                 360                 365

Arg Leu Leu Thr Arg Asp Leu Asn Cys Val Ala Ser Gly Asp Leu Cys
    370                 375                 380

Val
385

-continued

```
<210> SEQ ID NO 54
<211> LENGTH: 387
<212> TYPE: PRT
<213> ORGANISM: Artificial sequence
<220> FEATURE:
<223> OTHER INFORMATION: Synthetic

<400> SEQUENCE: 54

Met Ala Arg Leu Cys Ala Phe Leu Met Thr Leu Leu Val Met Ser Tyr
1               5                   10                  15

Trp Ser Thr Cys Ser Leu Gly Cys Asp Leu Pro Gln Thr His Asn Leu
            20                  25                  30

Arg Asn Lys Arg Ala Leu Thr Leu Leu Val Gln Met Arg Arg Leu Ser
        35                  40                  45

Pro Leu Ser Cys Leu Lys Asp Arg Lys Asp Phe Arg Phe Pro Gln Glu
    50                  55                  60

Lys Val Asp Ala Gln Gln Ile Gln Asn Ala Gln Ala Ile Pro Val Leu
65                  70                  75                  80

Gln Glu Leu Thr Gln Gln Val Leu Asn Ile Phe Thr Ser Lys Asp Ser
                85                  90                  95

Ser Ala Ala Trp Asp Ala Ser Leu Leu Asp Ser Phe Cys Asn Asp Leu
            100                 105                 110

His Gln Gln Leu Asn Asp Leu Lys Ala Cys Val Met Gln Glu Val Gly
        115                 120                 125

Val Gln Glu Pro Pro Leu Thr Gln Glu Asp Tyr Leu Leu Ala Val Arg
    130                 135                 140

Thr Tyr Phe His Arg Ile Thr Val Tyr Leu Arg Glu Lys Lys Arg Ser
145                 150                 155                 160

Pro Cys Ala Trp Glu Val Val Arg Ala Glu Val Trp Arg Ala Met Tyr
                165                 170                 175

Ser Ser Ala Lys Leu Pro Ala Arg Leu Ser Glu Glu Lys Glu Ala Ser
            180                 185                 190

Gly Ser Ser Gly Gly Ser Ser Gly Thr Ser Gly Ser Ser Gly Gly Ser
        195                 200                 205

Ser Gly Thr Ser Thr Asp Pro Val Pro Arg Ala Thr Arg Leu Pro Val
    210                 215                 220

Glu Ala Lys Asp Cys His Ile Ala Gln Phe Lys Ser Leu Ser Pro Lys
225                 230                 235                 240

Glu Leu Gln Ala Phe Lys Lys Ala Lys Asp Ala Ile Glu Lys Arg Leu
                245                 250                 255

Leu Glu Lys Asp Met Arg Cys Ser Ser His Leu Ile Ser Arg Ala Trp
            260                 265                 270

Asp Leu Lys Gln Leu Gln Val Gln Glu Arg Pro Lys Ala Leu Gln Ala
        275                 280                 285

Glu Val Ala Leu Thr Leu Lys Val Trp Glu Asn Met Thr Asp Ser Ala
    290                 295                 300

Leu Ala Thr Ile Leu Gly Gln Pro Leu His Thr Leu Ser His Ile His
305                 310                 315                 320

Ser Gln Leu Gln Thr Cys Thr Gln Leu Gln Ala Thr Ala Glu Pro Lys
                325                 330                 335

Pro Pro Ser Arg Arg Leu Ser Arg Trp Leu His Arg Leu Gln Glu Ala
            340                 345                 350

Gln Ser Lys Glu Thr Pro Gly Cys Leu Glu Asp Ser Val Thr Ser Asn
        355                 360                 365
```

Leu Phe Arg Leu Leu Thr Arg Asp Leu Lys Cys Val Ala Ser Gly Asp
            370                 375                 380

Gln Cys Val
385

<210> SEQ ID NO 55
<211> LENGTH: 379
<212> TYPE: PRT
<213> ORGANISM: Artificial sequence
<220> FEATURE:
<223> OTHER INFORMATION: Synthetic

<400> SEQUENCE: 55

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn Ala Ser Gly Ser Ser Gly Gly Ser Ser Gly
            180                 185                 190

Thr Ser Gly Ser Ser Gly Gly Ser Gly Thr Ser Thr Asp Pro Val
        195                 200                 205

Pro Arg Ala Thr Arg Leu Pro Val Glu Ala Lys Asp Cys His Ile Ala
    210                 215                 220

Gln Phe Lys Ser Leu Ser Pro Lys Glu Leu Gln Ala Phe Lys Lys Ala
225                 230                 235                 240

Lys Asp Ala Ile Glu Lys Arg Leu Leu Glu Lys Asp Met Arg Cys Ser
                245                 250                 255

Ser His Leu Ile Ser Arg Ala Trp Asp Leu Lys Gln Leu Gln Val Gln
            260                 265                 270

Glu Arg Pro Lys Ala Leu Gln Ala Glu Val Ala Leu Thr Leu Lys Val
        275                 280                 285

Trp Glu Asn Met Thr Asp Ser Ala Leu Ala Thr Ile Leu Gly Gln Pro
290                 295                 300

Leu His Thr Leu Ser His Ile His Ser Gln Leu Gln Thr Cys Thr Gln
305                 310                 315                 320

Leu Gln Ala Thr Ala Glu Pro Lys Pro Pro Ser Arg Arg Leu Ser Arg
                325                 330                 335

-continued

```
Trp Leu His Arg Leu Gln Glu Ala Gln Ser Lys Glu Thr Pro Gly Cys
            340                 345                 350

Leu Glu Asp Ser Val Thr Ser Asn Leu Phe Arg Leu Leu Thr Arg Asp
        355                 360                 365

Leu Lys Cys Val Ala Ser Gly Asp Gln Cys Val
    370                 375
```